United States Patent
Anantaneni et al.

(10) Patent No.: US 8,580,723 B2
(45) Date of Patent: *Nov. 12, 2013

(54) PROCESS COMPOSITIONS AND PRODUCTION OF ACYL ALKYLISETHIONATE COMPOSITIONS

(75) Inventors: Prakasa R. Anantaneni, The Woodlands, TX (US); George A. Smith, The Woodlands, TX (US); Martin J. Renner, Conroe, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 138 days.

This patent is subject to a terminal disclaimer.

(21) Appl. No.: 13/330,782

(22) Filed: Dec. 20, 2011

(65) Prior Publication Data

US 2012/0094890 A1 Apr. 19, 2012

Related U.S. Application Data

(62) Division of application No. 12/298,635, filed as application No. PCT/US2007/010519 on May 1, 2007, now Pat. No. 8,105,993.

(60) Provisional application No. 60/797,055, filed on May 2, 2006.

(51) Int. Cl.
  *A61K 8/00* (2006.01)

(52) U.S. Cl.
  USPC .......... 510/156; 510/424; 510/426; 510/492; 510/127

(58) Field of Classification Search
  None
  See application file for complete search history.

(56) References Cited

U.S. PATENT DOCUMENTS

| | | | |
|---|---|---|---|
| 5,384,421 A | 1/1995 | Day et al. | |
| 5,519,154 A | 5/1996 | Naylor | |
| 6,069,262 A | 5/2000 | Walele et al. | |
| 8,008,239 B2 | 8/2011 | Anantaneni | |
| 8,105,993 B2 * | 1/2012 | Anantaneni et al. | .......... 510/127 |

FOREIGN PATENT DOCUMENTS

WO 94/09763 5/1994

* cited by examiner

*Primary Examiner* — Necholus Ogden, Jr.
(74) *Attorney, Agent, or Firm* — Monique M. Raub

(57) ABSTRACT

Methods and compositions are provided for forming ester based compositions. The ester based compositions may be used in consumer products. In one aspect, a method is provided for producing acyl alkylisethionate esters by the esterification of a sulfonate composition having two or more sulfonate isomers with fatty acid(s). In another aspect, a method is provided for forming an ester based composition including a blend of acyl alkylisethionate and acylisethionate esters.

19 Claims, 1 Drawing Sheet

PROCESS COMPOSITIONS AND PRODUCTION OF ACYL ALKYLISETHIONATE COMPOSITIONS

CROSS-REFERENCES TO RELATED APPLICATIONS

This application is a divisional of currently pending U.S. patent application Ser. No. 12/298,635, which is the National Phase of International Application PCT/US2007/010519 filed May 1, 2007 which designated the U.S. and which claims priority to U.S. application Ser. No. 10/586,027 filed Jul. 13, 2006 and U.S. Provisional App. Ser. No. 60/797,055 filed May 2, 2006. The noted applications are incorporated herein by reference.

BACKGROUND OF THE INVENTION

1. Field of the Invention

The present invention is directed to the preparation of acyl alkylisethionate ester salts, intermediates thereof, and the application of the same in consumer products.

2. Background of the Related Art

Acyl alkylisethionate esters are anionic surfactants that may be used in a variety of personal care cleansers such as soaps, cosmetic compositions, and cleaning formulations. One acyl isethionate ester, sodium cocoyl isethionate ("SCI"), is an ester currently used extensively in soap-combi bars (i.e., syndet bars) due to its low solubility in water and mildness on the skin, as compared to harsher fatty acid soap bars.

U.S. Pat. No. 5,384,421 to Day et al. discloses a method for making salts of acyl isethionates using a direct esterification of a fatty acid with one or more salts of a selected hydroxy-alkanesulfonic acid in the presence of a catalyst selected from the group described therein.

U.S. Pat. No. 6,069,262 to Walele et al. discloses a composition of matter of fatty acids of hydroxylalkyl sulfonate salts, in particular sodium cocoyl isethionate (SCI) and process for preparing the same.

Due mainly to its low water solubility, SCI is not suitable for use in liquid cleansers. One method for improving SCI's limited water solubility is to combine SCI with other surfactants such as taurate, amphoacetates and betaines. This combination of surfactants, however, produces relatively hazy solution, which tend to separate during storage.

Therefore, it would be desirable to produce acyl isethionate esters that are highly water soluble, hydrolytically-stable and non-irritating for use in aqueous as well as non-aqueous consumer products such as personal care cleansers.

SUMMARY OF THE INVENTION

The present invention includes certain preferred combinations of the acyl alkylisethionate ester compositions, processes for forming the acyl alkylisethionate ester compositions, and additional processing thereof into useful articles. The present invention also includes alkyl-substituted hydroxyalkyl sulfonates and methods of preparing alkyl-substituted hydroxyalkyl sulfonates.

One embodiment of the invention is a process comprising: providing at least one alkylene oxide having between 2 and 8 carbon atoms; providing an aqueous solution comprising a bi-sulfite anion. The alkylene oxide is contacted with the aqueous solution while maintaining a pH between about 5 and about 10. A mixture is then formed of (i) a first isomer having the structure:

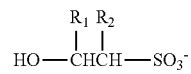

wherein $R_1$ and $R_2$ are straight chain or branched $C_1$ to $C_6$ alkyl groups, and (ii) a second isomer having the structure:

wherein $R_3$ and $R_4$ is a straight chain or branched $C_1$ to $C_6$ alkyl group. The molar ratio of the first isomer and the second isomer ranges from about 19:1 to about 1:19.

An alternative embodiment of the invention is a process comprising: providing at least one alkylene oxide having between 2 and 8 carbon atoms; providing an aqueous solution comprising a bi-sulfite anion. The alkylene oxide is contacted with the aqueous solution while maintaining a pH between about 5 and about 10. A mixture is formed of (i) a first isomer having the structure:

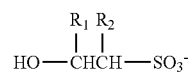

wherein $R_1$ is a straight chain or branched $C_1$ to $C_6$ alkyl group and $R_2$ is a hydrogen atom, and alternatively both $R_1$, $R_2$ are hydrogen (ii) a second isomer having the structure:

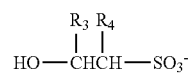

wherein $R_3$ is a hydrogen atom and $R_1$ is a straight chain or branched $C_1$ to $C_6$ alkyl group, and alternatively both $R_3$, $R_4$ are hydrogen.

The molar ratio of the first isomer and the second isomer ranges from about 19:1 to about 1:19.

An alternative embodiment of the invention is a process comprising: providing a hydroxide solution; providing sulfur dioxide; providing at least one alkylene oxide having between 2 and 8 carbon atoms per molecule. A mixture of the following is formed:

(i) a first isomer having the structure:

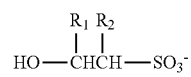

wherein $R_1$ is a straight chain or branched $C_1$ to $C_6$ alkyl group and $R_2$ is a hydrogen atom, and alternatively both $R_1$, $R_2$ are hydrogen.

(ii) a second isomer having the structure:

wherein $R_3$ is a hydrogen atom and $R_1$ is a straight chain or branched $C_1$ to $C_6$ alkyl group.

The mixture is formed while maintaining a pH of between about 7 and about 8; and alternatively both $R_3$, $R_4$ are hydrogen. The molar ratio of the first isomer and the second isomer is ranges from about 19:1 to about 4:1.

An alternative embodiment of the invention is a composition of matter, comprising:
a mixture of
(i) a first isomer having the structure:

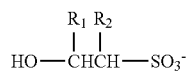

wherein $R_1$ is a straight chain or branched $C_1$ to $C_6$ alkyl group and $R_2$ is a hydrogen atom, and (ii) a second isomer having the structure:

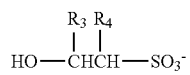

wherein $R_3$ is a hydrogen atom and $R_4$ is a straight chain or branched $C_1$ to $C_6$ alkyl group.

A molar ratio of the first isomer and the second isomer ranges from about 19:1 to about 4:1, and the composition is water soluble.

An alternative embodiment of the invention is a process for forming composition of matter, comprising: providing a mixture of alkylisethionates and isethionates at a molar ratio of alkylisethionates to isethionates between about 19:1 and about 4:1; reacting the mixture with a fatty acid having a carbon chain length between about 4 carbon atoms and about 25 carbon atoms; and producing a water soluble composition of isethionate esters having less than about 30% solubility.

An alternative embodiment of the invention is a composition comprising:
(i) a first ester anion having the structure:

wherein R is a functional group having between about 4 and about 25 carbon atoms; $R_1$ and $R_2$ are independently a straight chain or branched $C_1$ to $C_6$ alkyl group or a hydrogen atom, wherein if $R_1$ is the alkyl group then $R_2$ is the hydrogen, and if $R_2$ is the alkyl group then $R_1$ is the hydrogen; and (ii) a second ester anion having the structure:

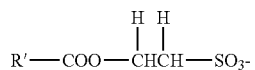

wherein R' is a hydrocarbon group having between about 4 and about 25 carbon atoms, and optionally
(iii) a third ester anion having the structure:

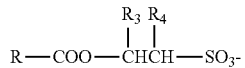

wherein R is a functional group having between about 4 and about 25 carbon atoms; $R_3$ and $R_4$ are independently a straight chain or branched $C_1$ to $C_6$ alkyl group or a hydrogen atom, wherein if $R_3$ is the alkyl group then $R_4$ is the hydrogen, and if $R_3$ is the alkyl group then $R_4$ is the hydrogen.

An alternative embodiment of the invention is a personal care cleanser comprising:
an acyl alkylisethionate ester composition having two or more esters according to the formula:

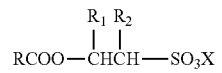

wherein at least a first ester comprises R having a hydrocarbon group having between about 4 and 25 carbon atoms, $R_1$ and $R_2$ each comprise a straight chain or branched $C_1$ to $C_6$ alkyl group or a hydrogen atom with at least one of $R_1$ or $R_2$ comprising the alkyl group and at least one of $R_1$ or $R_2$ comprising the hydrogen atom, and at least a second ester comprises R having a hydrocarbon group having between about 4 and 25 carbon atoms, $R_1$ comprises a hydrogen atom, $R_2$ comprises a hydrogen atom, and X for the first ester ion and the second ester ion are each selected from the group consisting of hydrogen, an alkali metal, an alkaline earth metal, zinc, aluminum, ammonium, ammonium ions substituted with one or more organic groups, and combinations thereof.

Weight percents disclosed herein are based on the total weight of the composition, unless otherwise specified or unless would otherwise be understand by one of ordinary skill in the art. Additionally, unless otherwise specified all pressures are absolute pressures based on the total weight of the composition, unless otherwise specified or unless would otherwise be understand by one of ordinary skill in the art. Moreover, all measurements disclosed herein are at standard temperature and pressure, at sea level on Earth, unless indicated otherwise.

BRIEF DESCRIPTION OF FIGURES

For a detailed understanding and better appreciation of the present invention, reference should be made to the following detailed description of the invention, taken in conjunction with the accompanying figures.

DETAILED DESCRIPTION OF THE INVENTION

Figure 1A:
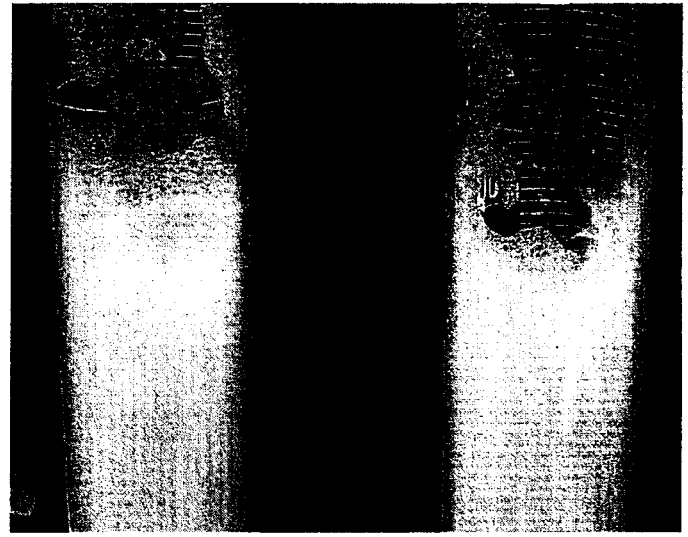
FIG. 1A depicts the foaming characteristics of SCMI.

The following is a detailed description of certain preferred combinations of the acyl alkylisethionate ester compositions, processes for forming the acyl alkylisethionate ester compositions, and additional processing thereof into useful articles. Those skilled in the art will appreciate that numerous modifications to these preferred embodiments may be made without departing from the scope of the invention. For example, while certain specific acyl alkylisethionate ester compositions are exemplified, other compositions are also contemplated. Additionally, while some products are discussed as uses for the composition, other uses, are also contemplated.

The present invention provides processes for forming acyl alkylisethionate ester compositions. The acyl alkylisethionate ester compositions generally have improved solubility and hydrolytic stability as compared to acyl isethionate compositions while retaining beneficial properties including, high-tight foaming, and non-irritating to human tissue. The acyl alkylisethionate ester compositions would be useful as primary or secondary surfactants in aqueous and non-aqueous consumer products such as personal care cleansers. The acyl alkylisethionate ester compositions may include isomeric acyl alkylisethionate esters, a blend of an acyl alkylisethionate ester and an acyl isethionates ester, or mixtures thereof. Salt derivatives of the esters described herein may also be used for the respective esters in forming the acyl alkylisethionate ester compositions.

An acyl alkylisethionate ester herein refers to an acyl isethionate ester in which at least one hydrogen atom on the alkyl moiety of the isethionate portion of the molecule is substituted with an alkyl group. For example, an alkyl group is substituted onto at least one carbon atom of the alkane sulfonate portion of the acyl isethionate ester. An acyl isethionate ester herein refers to an isethionate ester without an alkyl substitution, such as sodium cocoyl isethionate (SCI). In one embodiment of the invention, the acyl alkylisethionate ester has the following general formula (I):

wherein R is any hydrocarbon group having between 4 and 25 carbon atoms; $R_1$ and $R_2$ are each independently selected from the group consisting of hydrogen and a branched or straight aliphatic $C_1$ to $C_6$ alkyl group; and X is any cationic species present for charge neutrality such as hydrogen, ammonium and ammonium ions which are substituted with one or more organic groups, an alkali metal including sodium, potassium, and lithium, an alkaline earth metal including calcium and magnesium, zinc, aluminum, and combinations thereof. In a preferred embodiment, only one of $R_1$ and $R_2$ is a branched or straight aliphatic $C_1$ to $C_6$ alkyl group while the remaining $R_1$ or $R_2$ is hydrogen. The respective compounds having the aliphatic group on $R_1$, or alternatively, $R_2$ form the respective isomers of the compound of Formula (I). An example of a compound is sodium cocoyl methyl isethionate (SCMI).

In another example, the acyl alkylisethionate ester is an alkyl-substituted acylpropylsulfonate ester having the general formula (II):

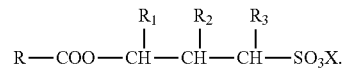

R may comprise any hydrocarbon group having between 4 and 25 carbon atoms. R is preferably selected from the group consisting of straight-chain hydrocarbon groups, branched hydrocarbon groups, saturated hydrocarbon groups, unsaturated hydrocarbon groups, and combinations thereof. $R_1$, $R_2$, and $R_3$ are each independently selected from the group consisting of hydrogen and a branched or straight aliphatic $C_1$ to $C_6$ alkyl group. In one preferred embodiment of the formula, one of $R_1$ and $R_2$ and $R_3$ is a branched or straight aliphatic $C_1$ to $C_6$ alkyl group while the remaining functional groups, $R_1$, $R_2$, or $R_3$, are hydrogen. Alternatively, two of $R_1$ and $R_2$ and $R_3$ are a branched or straight aliphatic $C_1$ to $C_6$ alkyl group while the remaining functional group, $R_1$, $R_2$, or $R_3$, is hydrogen. In another embodiment, $R_1$ and $R_2$ and $R_3$ are each a branched or straight aliphatic $C_1$ to $C_6$ alkyl group. In another embodiment, $R_1$ and $R_2$ and $R_3$ are each hydrogen. X may be any cationic species present for charge neutrality such as hydrogen, an alkali metal such as sodium, potassium and lithium, calcium, magnesium, zinc, aluminum, ammonium and ammonium ions which are substituted with one or more organic groups.

Isomeric acyl alkylisethionate esters of the present invention may be prepared by direct esterification of one or more alkyl-substituted isethionates, for example methyl-substituted isethionates. In an embodiment, isomeric acyl alkylisethionate esters of the present invention may be prepared by contacting two or more alkyl-substituted isethionates in the presence of a carboxylic acid. In another embodiment, isomeric acyl alkylisethionate esters of the present invention may be prepared by contacting one, two, or more alkyl-substituted isethionates and at least one sodium isethionate in the presence of a carboxylic acid. The isomeric alkyl-substituted isethionates may be prepared by reacting an alkylene oxide(s) with anions derived from a mineral acid, such as an aqueous solution of bisulfite anions. Preferred alkylene oxides have between 2 and 8 carbon atoms per molecule. The invention contemplates that alkylene oxides having 2 or more carbon atoms may be used. Examples of suitable alkylene oxides used in preparing the isethionates may include propylene oxide, ethylene oxide, butylene oxide, and combinations thereof.

The aqueous solution of bisulfite may have a concentration from about 10% to about 70% by weight, such as between about 20% and about 50%, for example, between about 30% and about 45%. The aqueous solution of bisulfite may include any alkali metal aqueous solution of bisulfite, such as sodium or potassium bisulfite. Additionally, the aqueous bisulfite solution may contain one or more cations such as sodium, potassium, lithium, magnesium, calcium, and ammonium ions are present in the aqueous bisulfite solution to maintain charge neutrality, and in fact any ion by which charge neutrality may be accomplished is suitably included in the aqueous solution, including mono-positive ions, di-positive ions, and triply positive ions. The cations may form salts with the anions formed during the reaction. For example, sodium alkylisethionates (SAI) may be produced from the presence of sodium ions in the aqueous solution. In an embodiment, the aqueous solution is comprised of sulfite ions and bi-sulfite ions. Preferably the aqueous solution comprises 25 wt. % to 99 wt. % sulfite ions and 1 wt. % to 75. wt % bi-sulfite ions. In another embodiment, the aqueous solution comprises 40 wt. % to 99 wt. % sulfite ions and 1 wt. % to 60 wt. % bi-sulfite ions. In an embodiment, the aqueous solution, comprising bi-sulfite ions or a combination of hydroxide solution and sulfur dioxide.

In one embodiment, the alkyl-substituted isethionate is an alley-substituted hydroxyethane sulfonate produced by the following reactions:

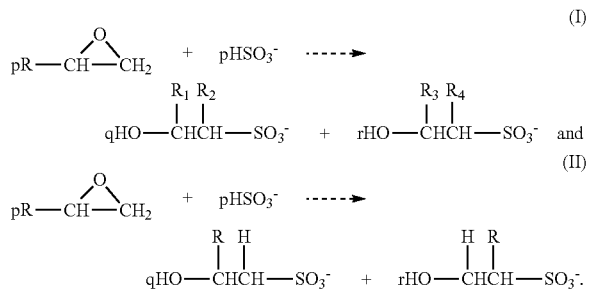

R is a $C_1$ to $C_6$ alkyl group, $R_1$ and $R_2$ are each independently selected from the group of hydrogen and a $C_1$ to $C_6$ alkyl group. In a preferred embodiment of a compound from reaction (I), only one of $R_1$ and $R_2$ is hydrogen while the other is a $C_1$ to $C_6$ alkyl group. $R_3$ and $R_4$ are each independently selected from the group of hydrogen and a $C_1$ to $C_6$ alkyl group. In a preferred embodiment of a compound from reaction (I), only one of $R_3$ and $R_4$ is hydrogen while the other is a $C_1$ to $C_6$ alkyl group. Q+r is equal to p for both reactions (I) and (II).

The respective presence of alkyl group (R) on the first and second carbon atoms, as shown in reaction (II), of the anions, may form substituted primary and secondary hydroxyl isomeric sulfonates. Preferably, the molar ratios of the substituted secondary hydroxyl carbon to substituted primary hydroxyl carbon at between about 19:1 to about 1:19, between about 19:1 and about 4:1, such as between about 17:3 and about 19:1, for example, about 15:1 to about 1:15. Preferably, propylene oxide, butylene oxide and oxides up to six carbon atoms are used to produce isomers containing primary hydroxyls and secondary hydroxyl sulfonates. The ratio may vary depending upon the reaction conditions and production of by products such as propylene glycol, butylene glycol, propoxylated/butoxylated sodium alkylisethionates, among others.

In one example of the reaction, propylene oxide is reacted with sodium bisulfite/sulfite to produce sodium 2-methyl 2-hydroxyethane sulfonate and/or sodium 1-methyl 2-hydroxyethane sulfonate or a mixture thereof. In another example butylene oxide is reacted with sodium bisulfite/sulfite to produce sodium 2-ethyl 2-hydroxyethane sulfonate and/or sodium 1-ethyl 2-hydroxyethane sulfonate or a mixture thereof.

Additionally, a mixture of alkyl-substituted isethionate may be formed by using one or more oxides. In one example, a mixture of propylene oxide and butylene oxide is reacted with sodium bisulfite/sulfite to produce sodium 2-methyl 2-hydroxyethane sulfonate, sodium 2-ethyl 2-hydroxyethane sulfonate, sodium 1-methyl 2-hydroxyethane sulfonate, and/or sodium 1-ethyl-2-hydroxyethane sulfonate, or mixtures thereof. In one example, a mixture of ethylene oxide, propylene oxide and/or butylene oxide may be used to generate a mixture of sodium alkylisethionate and sodium isethionate compounds.

The various oxides can be combined in any proportion by varying molar ratios to obtain the desired amounts of each alkyl-substituted hydroxyalkyl sulfonate. In one example, a preferred mixture of alkylisethionates and isethionates can be produced by mixing propylene oxide, and/or butylene oxide with ethylene oxide in any proportion containing ethylene oxide, propylene oxide, and/or butylene oxide, or a combination thereof. The oxide mixture produces isethionates, and isomeric mixtures of methylisethionates, and/or ethylisethionates, in the above reactions.

The alkyl-substituted isethionate may be used in the esterification process as follows to form an acyl alkylisethionate that is, completely water soluble sodium cocoyl alkylisethionate esters (SCAI) by reaction of SAI with fatty acids and a catalyst(s), and unlike pure SCI, water soluble to generate clear formulations for personal care applications.

During production of the alkyl-substituted isethionates, also referred herein as alkylisethionates, the pH of the reaction solution comprising the alkylene oxide and bisulfite may range from about 4 to about 10. A preferred pH of the reaction solution may be between about 5 to about 10. It is believed such a pH range will minimize side reactions and side products such as diols. In another preferred pH level, the pH of the reaction solution may be maintained optimally at a pH of about 7. It is believed that such a pH level will maximize production of alkyl-substituted isethionates having a high content of secondary ester link carbons. To maintain the pH of the reaction solution at a desired pH range during the entire reaction, a weak acid or buffering acid and/or more bisulfite may be added to the reaction solution as needed.

Alternatively a mixture of alkylisethionates could be made by forming the alkyl-substituted isethionates from respective oxides, such as propylene oxide and butylene oxide, separately and then combined into one mixture before the esterification process. The respective amount of the individual alkyl-substituted isethionates formed from the respective oxides may be determined for the esterification process to produce isethionates with desired properties, such as a desired viscosity or solubility. The use of a mixture of alkyl-substituted isethionates from reaction with the respective oxides has been observed to have lowered the melt point and improved homogeneity of the mixture at lower temperature, and decreased reaction times, of the products formed in the subsequent esterification process.

In an alternative embodiment, the alkyl-substituted isethionates are prepared by making the bisulfite/sulfite in situ by reacting a hydroxide solution, such as sodium hydroxide, with sulfur dioxide under pressure. Suitable hydroxide solution concentrations include 10, 25, and 50% by weight sodium hydroxide, alternatively the solution may comprises a sodium hydroxide concentration of from about 25% by weight to about 45% by weight. Suitable hydroxide solutions include potassium hydroxide, ammonium hydroxide, sodium hydroxide, or combinations thereof. In a preferred embodiment of the hydroxide solution, the hydroxide solution may comprise a 50% by weight sodium hydroxide solution. The alkylene oxide can be added concurrently or after to produce the corresponding isethionates and alkyl-substituted isethionates.

Furthermore, the temperature and pressure of the reaction solution during production of the alkyl-substituted isethionates may range between about 20° C. and about 200° C., such as between about 30° C. and about 95° C., for example between about 50° C. and about 80° C.; and from between about 0.00 psi to about 103 psi, such as between about 2.0 psi and about 7.0 psi, for example, between about 10.00 psi and about 50 psi respectively. The temperature and pressure of the reaction solution may be held constant during the entire reaction or one or both may be raised or lowered at any time for any time period to produce the desired alkyl-substituted isethionate.

Furthermore, the alkyl-substituted isethionates may be prepared as a liquid or in solid form. For example, the alkyl-substituted isethionates may first be prepared in liquid form then dried to form a powder. A preferred method of drying the alkyl-substituted isethionates is spray drying. For example, alkyl-substituted isethionates are prepared in liquid form by reacting propylene oxide and/or butylene oxide with sodium bisulfite. The liquid salts of the alkyl-substituted isethionate are then spray dried to the corresponding powder form. The alkyl-substituted isethionate powders have been found to be less hygroscopic and therefore easier to handle than non-alkyl-substituted isethionate powders making their transportation more efficient and less expensive. In addition, use of the alkyl-substituted isethionate powder allows for the elimination of a water removal step that is normally required when using a liquid alkyl-substituted isethionate during direct esterification.

The alkyl-substituted isethionates may then be used in producing the acyl alkylisethionate esters of the present invention by direct esterification of an alkyl-substituted isethionate mixture with a carboxylic acid. More than one alkyl-substituted isethionates mixture and/or more than one carboxylic acid may be used in the esterification reaction. Esterification occurs by mixing alkyl-substituted isethionate with carboxylic acids and optionally an esterification catalyst under esterification conditions. The alkyl-substituted isethionate can be present as the salt of the alkyl-substituted isethionate or in its acidic form. Alternatively, a composition of alkyl-substituted isethionate and isethionate may also be used in the esterification process.

Esterification for one embodiment may occur according to the reaction (III):

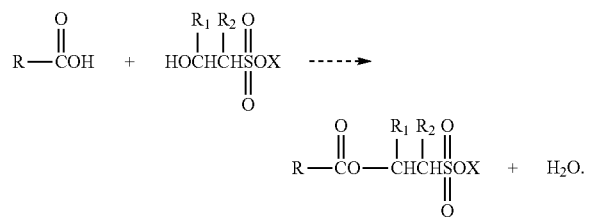

R is any hydrocarbon group having between about 4 and about 25 carbon atoms. The hydrocarbon group may include straight-chain, branched, saturated, unsaturated hydrocarbon groups, and combinations thereof. $R_1$ and $R_2$ may each independently be hydrogen or an alkyl group having 1 to 6 carbons, $C_1$ to $C_6$ alkyl. In a preferred embodiment of the reaction, at least one of $R_1$ and $R_2$ is hydrogen and at least one of at least one of $R_1$ and $R_2$ is a $C_1$ to $C_6$ alkyl group. X is a cationic species present for charge neutrality, Suitable cationic species are selected from the group consisting of hydrogen, alkali metals, alkaline earth metals, zinc, aluminum, ammonium, and ammonium ions which are substituted with one or more organic groups, and combinations thereof. When X is hydrogen, the alkyl-substituted alkylisethionic acid is present, which we have surprisingly found to be catalytic during esterification. X can be present as hydrogen by addition of any strong acid, however, it is most preferable to add the alkyl-substituted alkylisethionic acid itself in its pure form when it is added as an esterification catalyst.

In one embodiment of an acyl alkylisethionate ester composition, the composition includes a blend of isomeric acyl alkylisethionate esters with acyl isethionate esters. A composition including the blend of the isomeric acyl alkylisethionate esters and the acyl isethionate esters may be achieved by independently producing the respective esters and then mixing the esters in desired ratios to obtain a desired solubility. Alternatively, a composition including a blend of the isomeric acyl alkylisethionate esters with acyl isethionate esters may be achieved by blending alkyl-substituted isethionate and isethionate precursors, such as sodium alkylisethionate and sodium isethionate, respectively, prior to esterification as described herein. In either composition formation process, the molar ratio of isomeric acyl alkylisethionate esters to acyl isethionate esters in the composition may be between about 0.5:9.5 and about 9.5:0.5, such as between about 3:7 and about 7:3. Alternatively, a mixture of isomeric acyl alkyl-isethionate esters, as described herein, may be substituted for the isomeric in the composition described above.

The acyl isethionate esters have the formula (IV):

R is any hydrocarbon group having between 4 and 25 carbon atoms. R is preferably selected from the group consisting of straight-chain hydrocarbon groups, branched hydrocarbon groups, saturated hydrocarbon groups, unsaturated hydrocarbon groups, and combinations thereof. X may be any cationic species present for charge neutrality such as hydrogen, ammonium and ammonium ions which are substituted with one or more organic groups, an alkali metal including sodium, potassium, and lithium, an alkaline earth metal including calcium and magnesium, zinc, aluminum, and combinations thereof. An example of a compound is sodium cocoyl isethionate ester (SCI).

In one embodiment of the esterification reaction, isethionates may be included with alkyl-substituted isethionates to co-produce acyl isethionate esters from the isethionates with the production of the acyl alkylisethionate esters from alkyl-substituted isethionates during the same reaction process. For example, sodium cocoyl isethionate esters and sodium cocoyl alkylisethionates may be produced from an esterification reaction using sodium isethionates and sodium alkylisethionates as reactants with the carboxylic acid. In a mixed isethionate and alkyl-substituted isethionate reaction, the ratio of isethionate to alkyl-substituted isethionate may be between about 0.5:9.5 and about 9.5:0.5, such as between about 3:7 and about 7:3. The ratios are illustrative, and the invention contemplates that the ratio of the respective components may be varied to produce compounds having desired physical properties, such as solubility. Suitable isethionate compounds include 10, 20, 30 wt % isethionate and the balance is alkyl-substituted isethionate. The ratio are illustrative, and the invention contemplates that the ratio of the respective components may be varied to produce compounds having desired physical properties, such as solubility.

It has been surprisingly found that a mixed isethionate and alkyl-substituted isethionate esterfication reaction can occur at a lower temperature, at about 200° C. for a SI and SMI reaction, than the individual isethionate components, about 220° C. to about 250° C. for SMI and SI esterification reactions.

The carboxylic acids employed in producing the esters of the present invention have the general formula (IV):

R—COOH where R is any hydrocarbon group having between about 4 to about 25 carbon atoms. The R hydrocarbon group can be saturated or unsaturated, and straight-chain, branched, and combinations thereof. Generally, an excess of carboxylic acid is used in producing the esters of the present invention. Thus, the amount of carboxylic acid used may range from a mole ratio of carboxylic acid to isethionate of 1.5:1 to 1.1:1. However, a mole ratio range of carboxylic acid to isethionate as high as 2:1 to as low as 0.9:1 may be used if desired.

Examples of carboxylic acids suitable for use in the present invention include: coco acid; butyric acid; hexanoic acid; caproic acid; caprylic acid; capric acid; lauric acid; myristic acid; palmitic acid; palmitoleic acid; stearic acid; oleic acid; linoleic acid; arachidic acid; gadoleic acid; arachidonic acid; (EPA); behinic acid; eruic acid; (DHA); lignoceric acid; naturally occurring fatty acids such as coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures of any of the foregoing.

Those skilled in the art will appreciate that fatty acids obtained from naturally occurring sources are mixtures of acids having various carbon chains of various lengths. Therefore, it is within the scope of this invention to use one or more naturally occurring fatty acids (including mixtures thereof), synthetic fatty acids (including mixtures thereof) and mixtures of both natural and synthetic fatty acids. Moreover, "coco acid" or "coco fatty acid" as used herein is a commercial fatty acid mixture containing a range of carboxylic acids having chain lengths of between about $C_8$ to $C_{18}$, and some saturation which may be removed by hydrogenation. Thus, hydrogenated coco acid is a mixture of carboxylic acids having $C_8$ to $C_{18}$ chain lengths, mostly lauric and myristic, together with some capric and caprylic acids, and contains very little, if any, unsaturation.

In producing an acyl alkylisethionate ester by the reaction of a carboxylic acid with an alkylisethionate, such as an alkyl-substituted hydroxyethane sulfonate, the carbon atom of the hydroxyethane sulfonate portion of the molecule connected to the oxygen atom of the ester linkage is herein referred to as the "ester link carbon atom." It has been surprisingly found that when the alkylisethionate contains a high degree of ester link carbons that are secondary carbon atoms, the hydrolytic stability of the final acyl alkylisethionate ester product is substantially increased. No similar increase in hydrolytic stability has been observed with regards to increasing the secondary carbon content of the other carbon atom bonded directly to the sulfur atom in the alkylisethionate. Therefore, it is highly desirable to produce an alkyl-substituted isethionate that permits an acyl alkylisethionate ester produced therefrom to possess as high a degree of ester link carbons which are secondary carbon atoms as possible.

Additionally, an esterification catalyst may be employed and combined with the alkyl-substituted isethionate and carboxylic acid. Esterification catalysts suitable for use include alkylisethionic acids, salts of hydroxyalkane sulfonates, methane sulfonic acid, p-toluene sulfonic acid, inorganic acids such as sulfuric acid, phosphoric acid, phosphorous acid, boric acid or their anhydrides, heavy metal salts such as zinc sulfate, zirconium sulfate, zinc isethionate, zinc alkylisethionates, zinc cocoate, zinc citrate, zinc borate, aluminum sulfate, titanium sulfate or tungsten phosphate, metal oxides such as zinc oxide, aluminum oxide, magnesium oxide, cerium oxide, zirconium oxide or lanthanum oxide, organic acids such as citric acid and glycolic acid, and also mixtures of two or more of these catalysts, and soaps formed from heavy metals and metal oxides. The esterification catalyst may be employed in an amount from 0.05 to 2% by weight, preferably from 0.05% to 1% by weight, based on total weight of the reactants.

In one embodiment, the acyl alkylisethionate ester is prepared using the acidic form of alkyl-substituted hydroxyethane sulfonate as the esterification catalyst. The alkyl-substituted hydroxyethane isethionic acid can be added in its pure form or a strong acid can be added to the reaction mixture containing carboxylic acid and salt of the alkyl-substituted hydroxyethane isethionate to convert the isethionate salt to the acidic form.

The dual use of the alkyl-substituted hydroxyethane sulfonate as both a reactant and a catalyst is preferred since there is no need to quench or to remove the catalyst, there is no catalyst residues so there is minimal change in the molecular weight distribution of the acyl alkylisethionate ester, manufacturing capital expenditures are reduced and processing time is decreased.

In general detail, the esterification reaction can be conducted by charging the carboxylic acid, alkyl-substituted isethionate and isethionate as necessary, and optionally the esterification catalyst under atmospheric pressure or vacuum to a reaction vessel. The reaction vessel is flushed thoroughly with dry inert gas, such as nitrogen. Direct esterification is carried out by heating the reaction mixture to the reaction temperature with stirring. The water that may be introduced into the reaction mixture with the starting components and the water that is formed as a result of the esterification reaction is discharged from the reaction vessel. In addition, it may be also be required to distill off some of the excess carboxylic acid during the course of the esterification reaction. The reaction time to complete esterification will vary from 1 to 12 hours depending on the reaction temperature, and if present, the amount of esterification catalyst. The final ester product can then be delivered in liquid or solid form, such as a solution, powder, flakes or paste, for use as a raw material in the formulation of personal care cleansers.

The esterification reaction may be performed in a reaction vessel under atmospheric pressure. However, to aid in water removal, mild vacuum (500-550 mm Hg) may be applied during commencement of the charging of the reactants or anytime during the reaction. Applying mild vacuum also allows for water removal without distilling of the carboxylic acid. Preferably, the vacuum applied is not allowed to drop below 500 mm Hg so as to prevent carboxylic acid distillation when such is not desired.

Generally, the reaction vessel is heated to a single reaction temperature range. However, the process can employ more than one reaction temperature range. For example, the reaction vessel may be heated to a first reaction temperature range and held at that temperature range for a period of time to remove water, then subsequently heated further to a second temperature range higher than the first and held for a period of time. The reaction temperature ranges employed during the esterification reaction may range from about 180° C. to about 240° C. However, it has been surprisingly found that if alkyl-substituted isethionic acid is used as the catalyst, the reaction temperature can be lowered to a temperature range of about 90° C. to about 180° C., preferably about 120° C. to about 160° C.

In one embodiment, the acyl alkylisethionate ester is produced by combining one or more carboxylic acids and one or more sodium salts of the alkyl-substituted isethionate with an alkyl-substituted isethionic acid catalyst to a reaction vessel. Additionally, an isethionate ester may be formed in situ with the acyl alkylisethionate ester as described herein. The reaction vessel is purged using nitrogen and the reaction mixture is heated at a first temperature range of about 120° C. to about 130° C. for 30 minutes to remove water from the reaction components. The reaction mixture is then subsequently heated to a range of about 140° C. to about 150° C. to start the esterification reaction. Mild vacuum (500-550 mm Hg) is applied during the esterification reaction to assist in removal of water and the reaction mixture is continually heated until the distilling over of water ceases. The vacuum can be adjusted during the reaction to prevent carboxylic acid from distilling over. After esterification is complete, the residual alkyl-1-substituted isethionic acid present as a catalyst may be neutralized with an alkali such as caustic, amine, ammonia or substituted ammonium compounds such as mono-, di-, and triamines, and alkanolamine such as ethanolamine. The excess fatty acid can be conveniently removed by vacuum distillation at temperatures and pressures varying from about 100° and about 250° C. and between about 1 and about 200 mm Hg to make the product substantially fatty acid free.

The acyl alkylisethionate esters according to the present invention produced from alkyl-substituted isethionates are much more hydrolytically stable than acyl isethionate esters produced from non-alkyl-substituted isethionates, such as SI.

Thus, it has been surprisingly found that by substituting hydrogen with $C_1$ to $C_6$ alkyl groups on one or both of the carbon atoms of the ethane sulfonate portion of an acyl alkylisethionate ester, hydrolytic stability and water solubility of the acyl alkylisethionate ester is dramatically improved. That is by providing a $C_1$ to $C_6$ on one or both of the carbon atoms of the isethionic acid (or isethionate salt) raw material used in producing the acylethylisethionate ester, the water solubility and hydrolytic stability of the modified ester is improved. This result is wholly unexpected in view of the common knowledge in the art that increasing the hydrocarbon character of a material generally results in a reduction of water solubility. As a result of this improved solubility and hydrolytic stability, the acyl alkylisethionates of the present invention are suitable for use in liquid personal care cleaners and not limited to soap bars.

In one embodiment of the reaction processes described herein, using the respective reactants herein, allow for the formation of acyl alkylisethionate ester compositions having both acyl isethionate esters and acyl alkylisethionate esters. For example, an acyl alkylisethionate ester composition may include of sodium cocoyl alkylisethionate isomeric esters (SCAI) and sodium cocoyl isethionates esters (SCI) from a blend of sodium isethionate (SI) and sodium alkylisethionate isomeric mixture (SAI). The blend of acyl isethionate esters and acyl alkylisethionate esters in a composition have been observed to have lowered the melt temperatures of ester products and the ester products remain liquid at considerably lower temperatures than individual esters. In addition, it has also been observed that blend of acyl isethionate esters and acyl alkylisethionate esters provide improved homogeneity of the mixture at lower temperature with decreased reaction times during the esterification process.

Additionally, the blending of isethionates and alkyl-substituted isethionates prior to the esterification process has been observed to result in a composition having water soluble isethionate esters. For example, the blending of water insoluble sodium cocoyl isethionates with sodium cocyl alkylisethionates has been observed to result in a composition having water soluble sodium cocyl isethionates. Additionally, this blending enhanced not only the solubility but also the processability of the isethionate esters by lowering the melt temperatures of the reactants which allows for lowering reaction temperatures. Additionally, the reaction mass is more homogeneous at a lower temperature due to the lower melt temperatures of the reactants, the reaction is faster and the esterification is far more complete than single ester processes. Thus, the blending of the respective isethionates improves the economics of the esterification process and ester products compared to the process and products in manufacturing pure component esters blending for formulation purposes.

For example, a blend of sodium isethionate (SI) with sodium alkylisethionates, particularly, sodium methyl and ethyl isethionates separately or mixtures was reacted with fatty acids (carboxylic acids) using a catalyst such as zinc oxide at between about 200° C. and about 225° C. The reaction was observed to have a much higher ester formation at lower temperatures between about 200° C. and about 225° C. compared to between about 240° C. and about 250° C. with the esters remaining liquids at lower temperatures without product degradation. It was also observed that the blends prevented the solids formation during the addition of isethionate solution to fatty acid at temperatures below 150° C. and reduced the amount of fatty acid distilled over into water layer during the esterification process. Also, the reaction time was observed to be reduced by 25% and at most 50% compared to single sodium alkylisethionates reactions.

It is believed that varying the level of each of the isethionate and alkylisethionate component for the esterification, can produce ester products with a desired water solubility. For example, by increasing the level of sodium methyl isethionate or sodium ethyl isethionate in a composition having sodium isethionate, the solubility of the resulting ester was observed to improve from almost no solubility of the sodium isethionate ester to almost 30% solubility when sodium isethionate ester is mixed with either sodium methyl isethionate or sodium ethyl isethionate esters. More specifically, a composition of sodium cocoyl methyl isethionate (SCMI) and sodium cocoyl isethionate (SCI) resulted in water soluble isethionate esters when compared to water insoluble sodium cocoyl isethionate (SCI). The blending of sodium isethionate (SI) and sodium alkylisethionates (SAI) (especially, sodium methyl isethionate (P-salt), sodium ethyl isethionate, (B-salt) and reacting with fatty acids produced esters having improved water solubility compared to SCI from sodium isethionate. The ability to control the physical properties of the ester products, such as solubility, would allow for the manufacturing of tailor esters to suit customer needs.

Thus, the blend of esters as described herein gave unexpected or surprising results by improving solubility of isethionate esters, the alkylisethionate esters blends are milder than single component isethionates including SCI as shown in (Example 29 and Table 3 herein), the alkylisethionate esters blends have a lower melting point than single component esters, the blend of reactants to form the alkylisethionate esters blends have lower esterification reaction temperatures and shorter esterification reaction times with less product degradation.

Post-Esterification Processing:

Once formed, the acyl alkylisethionate ester compositions may be used as a surfactant or surface active agent in a variety of personal care cleansers. Personal care cleansers include, but are not limited to: liquid soaps, shampoos, shower gels, bubble baths, synthetic soap-combi-bars, acne washes, anti-dandruff shampoos, make-up removers, facial scrubs, baby wipes and children wipes. Thus, the compounds of the invention may be used in any personal care cleansing composition as may be known to those skilled in the art.

The acyl alkylisethionate ester compositions of the present invention may be used in personal care cleansers as a primary surfactant at levels ranging from 1% to 60% by weight. In addition, the acyl alkylisethionate ester compositions of the present invention may be blended with other surfactants and materials which are used in personal care cleansers at acyl alkylisethionate ester composition levels ranging up to about 60% by weight. To the extent that other surfactants may be used in combination with the acyl alkylisethionate ester compositions of the present invention in forming binary active systems, ternary active systems etc., the acyl alkylisethionate ester composition may comprise the majority of the surface active system (if more than one active is required) in which it is referred to as the primary surfactant, or it may comprise less than the majority of the surface active system in which it is referred to as the secondary surfactant.

Surfactants which may be used in combination with the acyl alkylisethionate ester compositions in forming the personal care cleanser may include amphoteric/zwitterionic surfactants, anionic surfactants, nonionic surfactants, cationic surfactants, and combinations thereof.

Amphoteric surfactants useful in the invention can broadly be described as a surface active agent containing at least one anionic and one cationic group and can act as either acids or bases depending on pH. Suitable amphoteric surfactants include aliphatic derivatives of heterocyclic secondary and tertiary amines in which the aliphatic radical may be straight or branched and wherein one of the aliphatic substituents contains from about 6 to about 20, preferably 8 to 18, carbon atoms and at least one contains an anionic water-solubilizing group, for example, a carboxyl group, a phosphonate group, a phosphate group, a sulfonate group, a sulfate group or combinations thereof.

Zwitterionic surfactants can be broadly described as surface active agents having a positive and negative charge in the same molecule which molecule is zwitterionic at all pHs. Examples of zwitterionic surfactants include betaines and sultaines. The zwitterionic compounds may contain a quaternary ammonium, quaternary phosphonium or a tertiary sulfonium moiety. The cationic atom in the quaternary compound can be part of a heterocyclic ring. Preferred zweitterionic compounds include at least one aliphatic group, straight chain or branched, containing from about 6 to 20, preferably 8 to 18, carbon atoms and at least one aliphatic substituent containing an anionic water-solubilizing group, for example, a carboxyl group, a phosphonate group, a phosphate group, a sulfonate group, a sulfate group or combinations thereof.

Examples of suitable amphoteric and zwitterionic surfactants include the alkali metal, alkaline earth metal, ammonium or substituted ammonium salts of alkyl amphocarboxyglycinates and alkyl amphocarboxypropionates, alkyl amphodipropionates, alkyl monoacetate, alkyl diacetates, alkyl amphoglycinates, alkyl amphopropionates, and combinations thereof. The alkyl includes an alkyl group having from 6 to about 20 carbon atoms. Other suitable surfactants include alkyliminomonoacetates, alkyliminidiacetates, alkyliminopropionates, alkyliminidipropionates, and alkylamphopropylsulfonates having between 12 and 18 carbon atoms, alkyl betaines and alkylamidoalkylene betaines and alkyl sultaines, alkylamidoalkylenehydroxy sulfonates, and combinations thereof.

Preferred anionic surfactants include compounds having a long chain hydrocarbon hydrophobic group and a hydrophilic group. The anionic surfactants may be in the form of salts such as carboxylate, sulfonate, sulfate or phosphate groups with sodium, potassium, calcium, magnesium, barium, iron, ammonium, amine salts, and combinations thereof, as the cationic portion of the salt.

Preferred anionic surfactants may also include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group.

Examples of anionic surfactants include water soluble salts of alkyl benzene sulfonates having between 8 and 22 carbon atoms in the alkyl group, alkyl ether sulfates having between 8 and 22 carbon atoms in the alkyl group and 2 to 9 moles ethylene oxide in the ether group, or combinations thereof. Other suitable anionic surfactants include alkyl sulfosuccinates, alkyl ether sulfosuccinates, olefin sulfonates, alkyl sarcosinates, alkyl monoglyceride sulfates and ether sulfates, alkyl ether carboxylates, paraffinic sulfonates, mono and di alkyl phosphate esters and ethoxylated derivatives, acyl methyl taurates, fatty acid soaps, collagen hydrosylate derivatives, sulfoacetates, acyl lactates, aryloxide disulfonates, sulfosucinamides, naphthalene-formaldehyde condensates, or combinations thereof. Aryl groups generally include one and two rings, alkyl generally includes from 8 to 22 carbon atoms and the ether groups generally range from 1 to 9 moles of ethylene oxide (EO) and/or propylene oxide (PO), preferably Ethylene oxide.

Further examples of suitable anionic surfactants include linear alkyl benzene sulfonates such as decylbenzene sulfonate, undecylbenzene sulfonate, dodecylbenzene sulfonate, tridecylbenzene sulfonate, nonylbenzene sulfate and the sodium, potassium, ammonium, triethanol ammonium and isopropyl ammonium salts thereof, or combinations thereof.

Nonionic surfactants may also be used in combination with the acyl alkylisethionate ester compositions of the present invention. The nonionic surfactant may be any of the known nonionic surfactants which are generally selected on the basis of compatibility, effectiveness and economy.

Examples of suitable nonionic surfactants include condensates of ethylene oxide with a hydrophobic moiety which has an average hydrophilic lipolytic balance (HLB) between about 8 to about 16, and preferably between about 10 and about 12.5. The surfactants include the ethoxylated primary or secondary aliphatic alcohols having from about 8 to about 24 carbon atoms, in either straight or branch chain configuration, with from about 2 to about 40, and preferably between about 2 and about 9 moles of ethylene oxide per mole of alcohol. Other suitable nonionic surfactants include the condensation products of from about 6 to about 12 carbon atoms alkyl phenols with about 3 to about 30, and preferably between about 5 to about 14 moles of ethylene oxide.

Preferred cationic surfactants include a cationic surfactant having at least one long chain alkyl group of about 10 to 24 carbon atoms is suitable for optional use in the present invention.

Alternatively, optional additives may be used in combination with acyl alkylisethionate ester compositions in formulating personal care cleansers. Optional additives include pH adjusting chemicals, phase regulants, detergent hydrotropes, defoamers, an inorganic or organic builder, or combinations thereof.

The pH adjusting chemicals, for example, lower alkanolamines such as monoethanolamine (MEA) and triethanolamine (TEA). Sodium hydroxide solutions may also be utilized as an alkaline pH adjusting agent. The pH adjusting chemicals function to neutralize acidic materials that may be present. Mixtures of more than one pH adjusting chemical can also be utilized.

Phase regulants (well known liquid detergent technology) may also be used as an optional additive. Phase regulants can be represented by lower aliphatic alcohols having from 2 to 6 carbon atoms and from 1 to 3 hydroxyl groups, ethers of diethylene glycol and lower aliphatic monoalcohols having from 1 to 4 carbon atoms and the like.

Examples of detergent hydrotropes include salts of alkylarylsulfonates having up to 3 carbon atoms in the alkyl group e.g., sodium, potassium, ammonium, and ethanolamine salts of xylene, toluene, ethylbenzene, cumene, and isopropylbenzene sulfonic acids.

Defoamers include high molecular weight aliphatic acids, especially saturated fatty acids and soaps derived from them, dyes and perfumes; fluorescent agents or optical brighteners; anti-redeposition agents, such as carboxymethyl cellulose and hydroxypropylmethyl cellulose; suspension stabilizing agents and soil release promoters such as copolymers of polyethylene terephthalate and polyoxyethylene terephthalate; antioxidants; softening agents and anti-static agents; photo activators and preservatives; polyacids, suds regulators, opacifiers, bacteriacide, and the like. Suds regulators may include, for example, alkylated polysiloxanes, opacifiers may include, for example, polystyrene, and bactericide may include, for example, butylated hydroxytoluene.

An inorganic or organic builder may optionally be added to the final composition. Examples of inorganic builders include water-soluble alkali metal carbonates, bicarbonates, silicates and crystalline and amorphous alumino silicates. Examples of organic builders include the alkali metal, alkaline metal, ammonium and substituted ammonium polyacetates, carboxylates, polycarboxylates, polyacetyl, carboxylates and polyhydroxy sulfonates. One example of a commonly used builder is sodium citrate.

The optional ingredients and optional surfactants can be added to the acyl alkylisethionate ester composition before, during or after formulation of the personal care cleanser. In addition, blends of the acyl alkylisethionate ester composition in combination with these optional ingredients and surfactants can be made directly for sale or for compounding to meet the needs of the user.

Thus, the acyl alkylisethionate esters of the present invention are useful in formulations which contain materials typically used by and known to those skilled in the art as being useful in formulating soap products, detergent products, and other cleansing-like products, particularly, but not limited, to personal care cleansers. For purposes of this invention, the words "material known to those skilled in the art as being useful in formulating soaps, detergents, and the like" means one or more of the materials selected from the group consisting of: fatty acids, alkyl sulfates, ethanolamines, amine oxides, alkali carbonates, water, ethanol, isopropanol, pine oil, sodium chloride, sodium silicate, polymers, alcohol alkoxylates, zeolites, perborate salts, alkali sulfates, enzymes, hydrotropes, dyes, fragrances, preservatives, brighteners, builders, polyacrylates, essential oils, alkali hydroxides, ether sulfates, alkylphenol ethoxylates, fatty acid amides, alpha olefin sulfonates, paraffin sulfonates, betaines, chelating agents, tallowamine ethoxylates, polyetheramine ethoxylates, ethylene oxide/propylene oxide block copolymers, alcohol ethylene oxide/propylene oxide low foam surfactants, methyl ester sulfonates, alkyl polysaccharides, N-methyl glucamides, alkylated sulfonated diphenyl oxide, and water soluble alkylbenzene sulfonates or alkyltoluene sulfonates, as the use of such in formulating soaps, detergents, and the cleansing-like products are known in the art.

In one embodiment, the acyl alkylisethionate ester compositions of the present invention may be present in facial and body cleansing compositions. These cleansing compositions may also comprise a fatty acid soap together with other non-soap surfactants, such as mild synthetic surfactants. Body and facial cleaning compositions may also generally include a moisturizer or emollient and polymeric skin feel and mildness aids. The compositions may further optionally include thickeners (e.g., magnesium aluminum silicate, carbopol), conditioners, water soluble polymers (e.g., carboxymethylcellulose), dyes, hydrotropes brighteners, perfumes, germicides, or combinations thereof. For liquid soap products, the acyl alkylisethionate composition herein may comprise between about 60 wt. % and about 90 wt. % of the acyl alkylisethionate compound, such as SCMI, and between about 10 wt. % to 40 wt. % of the acyl isethionate compound, such as SCI. For solid soap formulations, the acyl alkylisethionate composition herein may comprise between about 10 wt. % and about 40 wt. % of the acyl alkylisethionate compound, such as SCMI, and between about 60 wt. % to 90 wt. % of the acyl isethionate compound, such as SCI.

In another embodiment, the acyl alkylisethionate ester compositions of the present invention may be present in a shampoo. The shampoo composition may also comprise one or more other surfactants, a compound considered useful for treating dandruff, such as selenium sulfide, a suspending agent, an amide, nonionic polymer material for aiding in dispersing particles, nonvolatile silicone fluid, and a variety of other nonessential components suitable for rendering the composition more useful in various formulations, such as preservatives, viscosity modifiers, pH adjusting chemicals, perfumes, dyes, or combinations thereof.

In still another embodiment, the acyl alkylisethionate ester compositions of the present invention may be present in a light duty liquid detergent composition. The light duty liquid detergent composition may further include one or more other surfactants, opacifiers (e.g. ethylene glycol distearate), thickeners (e.g. guar gum), antimicrobial agents, anti-tarnish agents, heavy metal chelators (e.g. EDTA), perfumes, dyes, or combinations thereof.

In a further embodiment, the acyl alkylisethionate ester composition of the present invention may be present in a heavy duty liquid detergent composition. The heavy duty liquid detergent composition may also include one or more other surfactants, an electrolyte (i.e., water soluble salt), enzymes with or without stabilizers such as calcium ion, boric acid, propylene glycol and/or short chain carboxylic acids, conventional alkaline detergency builders, or combinations thereof.

In yet another embodiment, the acyl alkylisethionate ester composition may be present in a conditioner composition that comprises alkylamine compounds.

In a different embodiment, the acyl alkylisethionate ester compositions of the present invention may be present in a cosmetic composition. The cosmetic composition may further include at least one polymer thickening agent, one or more chemical preservatives or water activity depressants to prevent microbial spoilage, a sun-screening agent such as p-aminobenzoic acid, and a vehicle. The cosmetic composition medium can include any diluent, dispersant or carrier useful in ensuring an even distribution of the composition when applied to skin and may include water, an emollient such as an alcohol or oil, a propellant for example, trichloromethane, carbon dioxide or nitrous oxide, a humectant, a powder such as chalk, talc, and starch, or combinations thereof.

Advantages of the acyl alkylisethionate ester compositions described herein in the products described herein include improved solubility compared to acyl isethionate esters such as SCI, non-irritating properties of the acyl alkylisethionate ester compositions allow the composition to be used as a primary surfactant in place of traditional anionic surfactants such as sodium lauryl sulfate and sodium lauryl ether sulfate in personal care cleansers, and "sulfate-free" personal care cleansers can be made using the acyl alkylisethionate ester compositions without requiring the addition of taurates and sarcosinates needed for removing sulfates in current personal care cleansers.

The examples which now follow should be considered exemplary of the present invention, and are in no way limiting:

Experimental Data

The following viscosities were measured in a Brookfield Programmable DV-II+ viscometer.

The saponification value: mg of KOH per gram of material.
The respective acid value: mg of KOH per gram of material.
The correct sap value of the ester: saponification value—acid value.

Example 1

Preparation of Sodium Methyl Isethionate

A 3-gallon stainless steel-316 autoclave reactor with 9.40 pounds of 35% aqueous sodium bisulfite solution having a pH 6.5-7.0 and then nitrogen purged to exclude air. The reactor was then heated to about 70° C. and 1.0 pounds of propylene oxide was added to the reactor at a pressure of 60 psi. The reactants were allowed to react for about 30 minutes at a temperature of about 80° C. after which time the pressure in the reactor dropped to about 1 psi. The reaction was allowed to continue for 60 minutes at 80° C., cooled to 50° C., and the product solution was removed from the reactor and analyzed. Analysis showed the product solution having a pH of 13.50, <0.50% by weight propylene glycol, and both the 2-methyl, 2-hydroxy ethane 1-sulfonate and 1-methyl 2-hydroxy ethane 1-sulfonate isomers present.

A second 3-gallon stainless steel-316 autoclave reactor with 9.69 pounds of 35% aqueous sodium bisulfite solution having a pH 6.5-7.0 and then nitrogen purged to exclude air. The reactor was heated to about 70° C. and 1.5 pounds of propylene oxide was added to the reaction at a pressure of 60 psi. The reactants were allowed to react at 80° C. for 30 minutes after which time the pressure dropped to about 1 psi. The reaction was allowed to continue for 60 minutes at a temperature of 95° C. then cooled to 50° C. and the product solution was removed from the reactor and analyzed. Analysis showed the product solution having a pH of 14.00, about 3.0% by weight propylene glycol, and both the 2-methyl, 2-hydroxy ethane 1-sulfonate and 1-methyl 2-hydroxy ethane 1-sulfonate isomers present.

In a 170-gallon stainless steel-316 reactor equipped with an agitator, nitrogen line, oxide line, temperature probe and a pH probe, with 300 pounds of DI water and 120 pounds of 50% caustic solution. The reactor was pressure purged with nitrogen three times (40-0 psig). $SO_2$ was then passed through the reactor and solution with stirring to a pH of 7.0-7.50. The reactor was then heated to about 70°-75° C. and propylene oxide was added to the reactor at a rate of 0.50 lb/minute. The pH during the reaction controlled addition by the addition of small injections of $SO_2$. Furthermore, the addition of PO was slowed towards the end of the reaction to maintain good pH control. The reactants were allowed to digest at 95° C. for 4 hours. A total of 93 pounds of $SO_2$ and 90 pounds of propylene oxide were used during the entire reaction. The reactor was then opened to fume hood and stripped of any unreacted propylene oxide with a nitrogen purge for one hour. The reaction mixture was cooled to room temperature and discharged into drums. The clear and colorless product was analyzed and the results showed: 0.50% by weight propylene glycol and 50.20% by weight sodium methyl isethionate (with both 2-methyl, 2-hydroxy ethane 1-sulfonate and 1-methyl, 2-hydroxy ethane 1-sulfonate isomers present in about 15:1 molar ratio).

Example 2

Preparation of Sodium Ethyl Isethionate

A 3-gallon stainless steel-316 autoclave reactor with 9.69 pounds of 35% aqueous sodium bisulfite solution having a pH 6.5-7.0 and then nitrogen purged to exclude air. The reactor was then heated to about 70° C. and 2.6 pounds butylene oxide was added to the reactor at a pressure of 60 psi. The reactants were allowed to react for about 30 minutes at a temperature of about 80° C. after which time the pressure in the reactor dropped to about 1 psi. The reaction was allowed to continue for 60 minutes at 95° C. then cooled to 50° C. and the product solution was removed from the reactor. Upon cooling, shiny crystalline plates separated out of the product solution requiring water be added to dissolve the solids back into solution. The product solution was then analyzed and analysis showed the product solution having a pH of 14.00, about 3.0% by weight butylene glycol, and both the 2-ethyl, 2-hydroxy ethane 1-sulfonate and 1-ethyl 2-hydroxy ethane 1-sulfonate isomers present.

A second 3-gallon stainless steel-316 autoclave reactor with 9.69 pounds of 35% aqueous sodium bisulfite solution having a pH 5.0-5.5 and then nitrogen purged to exclude air. The reactor was heated to about 70° C. and 2.6 pounds of butylene oxide was added to the reaction at a pressure of 60 psi. The reactants were allowed to react at 80° C. for 30 minutes after which time the pressure dropped to about 1 psi. The reaction was allowed to continue for 60 minutes at a temperature of 95° C. then cooled to 50° C. and the product solution was removed from the reactor. Upon cooling, shiny crystalline plates separated out of the product solution requiring water be added to dissolve the solids back into solution. The product solution was then analyzed and analysis showed the product solution having a pH of 14.00, about 13.0% by weight butylene glycol, and both the 2-ethyl, 2-hydroxy ethane 1-sulfonate and 1-ethyl 2-hydroxy ethane 1-sulfonate isomers present in about 14.8:1 molar ratio.

Example 3

Preparation of Sodium Cocoyl ($C_8$ to $C_{18}$) Methyl Isethionate Ester

A laboratory reactor (500 ml round bottom flask equipped with a mechanical stirrer, an addition funnel, a condenser, a thermocouple and gas sparging provision) was initially charged with 212 grams (0.98 moles) of a carboxylic acid (hydrogenated coco acid C-110, P&G Chemicals, Cincinnati, Ohio). Also added to the reactor was a total of 165 grams (1.0 mole, solid) of sodium methyl isethionate containing a mixture of the sodium salts of 2-methyl, 2-hydroxy ethane 1-sulfonate and 1-methyl, 2-hydroxy ethane 1-sulfonate. 5.00 grams of the corresponding zinc methylisethionate, in the same isomer proportions as above, was added as a catalyst. The reactor was flushed thoroughly with dry nitrogen and heated to 120°-130° C. for 30 minutes to remove any water from the sodium methyl isethionate. The temperature of the reactor contents was then raised to 200° C. for 6 hours after which time excess fatty acid is removed by distillation under vacuum at 10 mm Hg to acceptable fatty acid levels (<10%) and the product mixture contains 80% by weight of the corresponding esters suitable for blending into a personal care cleansing composition.

In a second laboratory reactor (500 ml round bottom flask equipped with a mechanical stirrer, an addition funnel, a condenser, a thermocouple, and gas sparging provision) was added 131.5 grams (0.625 moles) of a carboxylic acid (Coconut fatty acid C-110, P&G Chemicals, Cincinnati, Ohio), a total of 82.5 grams (0.5 moles solids) of sodium methyl isethionate containing a mixture of the sodium salts of 2-methyl, 2-hydroxy ethane 1-sulfonate and 1-methyl 2-hydroxy ethane 1-sulfonate, and 2.2 grams of zinc citrate as a catalyst. The reactor is flushed thoroughly with dry nitrogen and the solution is heated at 220° C. for 6 hours after which time excess fatty acid is removed by distillation under vacuum at 10 mm Hg to acceptable fatty acid levels (<10%) and the product solution is cooled to 160° C.-170° C. The liquid product is removed from the reactor and analyzed and the results showed a product containing 81.5% by weight of the corresponding esters suitable for blending into a personal care cleansing composition, 12.0% by weight unreacted carboxylic acid, and 3.9% by weight unreacted sodium methyl isethionate.

Example 4

Preparation of Sodium Capryloyl/Caproyl ($C_8$ to $C_{10}$) Methyl Isethionate Ester In a laboratory reactor (500 ml round bottom flask equipped with a mechanical stirrer, an addition funnel, a condenser, a thermocouple, and gas sparging provision) 118 grams (0.75 moles) of a carboxylic acid (fatty acid C810, P&G Chemicals, Cincinnati, Ohio) and to the reactor was added a total of 82 grams (0.5 moles solids) of sodium methyl isethionate containing a mixture of the sodium salts of 2-methyl, 2-hydroxy ethane 1-sulfonate and 1-methyl 2-hydroxy ethane 1-sulfonate. 2.2 grams of zinc citrate was added to the mixture as a catalyst. The reactor was flushed thoroughly with dry nitrogen and the reactants heated at 220° C. for 6 hours after which time the product was cooled to 160° C.-170° C. The liquid product was removed from the reactor and analyzed and the results showed the white solid had a saponification value of 186, actives by two phase titration 2.54 meq/g and containing 86.7% by weight of the corresponding esters suitable for blending into a personal care cleansing composition, 6.7% by weight unreacted carboxylic acid, and 6.5% by weight unreacted sodium methyl isethionate with isomer ratio of secondary vs. primary hydroxyl in 39:1, a clear indication of, as expected, preferential esterification of primary hydroxyl over secondary in the methyl isethionate mixture.

Example 5

Preparation of Sodium Caproyl ($C_{10}$) Methyl Isethionate Ester

In a laboratory reactor (500 ml round bottom flask equipped with a mechanical stirrer, an addition funnel, a condenser, a thermocouple, and gas sparging provision) 108 grams (0.625 moles) of a carboxylic acid (fatty acid C-1095, P&G Chemicals, Cincinnati, Ohio) and to the reactor was added a total of 82.5 grams (0.5 moles solids) of sodium methyl isethionate containing a mixture of the sodium salts of 2-methyl, 2-hydroxy ethane 1-sulfonate and 1-methyl 2-hydroxy ethane 1-sulfonate. 1.9 grams of zinc citrate was added to the mixture as a catalyst. The reactor was flushed thoroughly with dry nitrogen and the reactants heated to 220° C. for 6 hours after which time the product was cooled to 160° C.-170° C. The liquid product was removed from the reactor and analyzed and the resulting white solid contained 82.5% by weight of the corresponding ester suitable for blending into a personal care cleansing composition, 7.7% by weight unreacted carboxylic acid, and 7.4% by weight unreacted sodium methyl isethionate.

Example 6

Preparation of Sodium Lauroyl ($C_{12}$) Methyl Isethionate Ester

In a laboratory reactor (500 ml round bottom flask equipped with a mechanical stirrer, an addition funnel, a condenser, a thermocouple, and gas sparging provision) 125 grams (0.625 moles) of a carboxylic acid (fatty acid C1299, P&G Chemicals, Cincinnati, Ohio) and to the reactor was added a total of 83 grams (0.5 moles solids) of sodium methyl isethionate containing a mixture of the sodium salts of 2-methyl, 2-hydroxy ethane 1-sulfonate and 1-methyl 2-hydroxy ethane 1-sulfonate. 2.2 grams of zinc citrate was added to the mixture a' a catalyst. The reactor was flushed thoroughly with dry nitrogen and the reactants heated to 220° C. for 6 hours after which time the liquid product was cooled to 160° C.-170° C. and poured into a one liter beaker. The resulting white solid was removed from the reactor and analyzed and the results showed a product containing 82.0% by weight of the corresponding ester suitable for blending into a personal care cleansing composition, 15.6% by weight reacted carboxylic acid, and 3.9% by weight unreacted sodium methyl isethionate.

Example 7

Preparation of Sodium Cocoyl (C12-$C_{12}$) Methyl Isethionate Ester

In a laboratory reactor (500 ml round bottom flask equipped with a mechanical stirrer, an addition funnel, a condenser, a thermocouple, and gas sparging provision) 137.5 grams (0.625 moles) of a carboxylic acid (fatty acid Emery 627, Cognis, Cincinnati, Ohio) and to the reactor was added a total of 85 grams (0.5 moles solids) of sodium methyl isethionate (95% by weight) containing a mixture of the sodium salts of 2-methyl, 2-hydroxy ethane 1-sulfonate and 1-methyl 2-hydroxy ethane 1-sulfonate. 1.2 grams of zinc citrate was added to the mixture as a catalyst. The reactor was flushed thoroughly with dry nitrogen and the reactants heated to 220° C. for 6 hours after which time the product solution was cooled to 160° C.-170° C. and poured into a one liter beaker. The white solid was removed from the beaker and analyzed and the results showed a product containing 82.2% by weight of the corresponding esters suitable for blending into a personal care cleansing composition, and 7.9% by weight unreacted carboxylic acid.

Example 8

Preparation of Sodium Cocoyl ($C_8$-$C_{18}$) Methyl Isethionate Ester

In a laboratory reactor (2000 ml round bottom flask equipped with a mechanical stirrer, an addition funnel, a condenser, a thermocouple, and gas sparging provision) 780 grams (3.75 moles) of a carboxylic acid (fatty acid Emery 626, Cognis, Cincinnati, Ohio) and 6.34 grams of zinc oxide (ZnO, 0.50 wt. %) were charged into the reactor, heated, and stirred mechanically to a temperature of 170-175° C. Sodium methyl isethionate solution in water (sulfonic SMI, 1040 grams, 47%, 3.0 moles) was added slowly over 60-70 minutes at a rate that keeps the mixture completely liquid. Water was distilled over from the reaction mixture as sulfonic SMI addition continued. After the addition of sulfonic SMI was completed, the reaction mixture was heated slowly over 30-45 minutes to 225° C. and continued for 4 hours. The reaction mixture becomes completely homogeneous around 210-215° C. The excess fatty acid was stripped by dry nitrogen purge for 2-3 hours to a desired fatty acid level, below 10%, preferably 6-8%. It was very important to keep air away from the hot reaction mixture to prevent color formation. The viscous and hot reaction product was poured into a 2-liter beaker under nitrogen and allowed it to cool to room temp. A total 995 grams of light yellow waxy solid ester was obtained. Acid value of this ester was 19.55, i.e., 7.25% and ester's correct sap value of 135.92, i.e., 85.27% and estimated unreacted surfonic SMI was 7.20%

Example 9

Preparation of Sodium Cocoyl ($C_8$-$C_{18}$) Ethyl Isethionate Ester

In a laboratory reactor (2000 ml round bottom flask equipped with a mechanical stirrer, an addition funnel, a condenser, a thermocouple, and gas sparging provision) 800 grams (3.85 moles) of a carboxylic acid (fatty acid Emery 626, Cognis, Cincinnati, Ohio) and 7.00 grams of zinc oxide (ZnO, 0.50 wt. %) and 528 g of sodium ethyl isethionate solid (3.00 moles) to the reactor and heated slowly with stirring mechanically under nitrogen to a temperature of 200-225° C. over 60-70 minutes and continued for 4 hours. The reaction mixture becomes completely homogeneous around 210-215° C. The excess fatty acid was stripped by dry nitrogen purge for 2-3 hours to a desired fatty acid level, below 10%, preferably 6-8%. It was very important to keep air away from the hot reaction mixture to prevent color formation. The viscous and hot reaction product was poured into a 2-liter beaker under nitrogen and allowed it to cool to room temp. A total 1100 grams of colorless waxy solid ester was obtained. Acid value of this ester was 22.80, i.e., 8.62% and ester's correct sap value of 127.10, i.e., 83.83% and estimated unreacted surfonic SMI was 7.20%.

Example 10

Preparation of Sodium Cocoyl ($C_8$-$C_{18}$) Methyl Isethionate Ester

In a laboratory reactor (2000 ml round bottom flask equipped with a mechanical stirrer, an addition funnel, a condenser, a thermocouple, and gas sparging provision) 780 grams (3.75 moles) of a carboxylic acid (fatty acid C-101, P&G, Cincinnati, Ohio) and 6.30 grams of zinc oxide (ZnO, 0.50 wt. %) were charged into the reactor, heated, and stirred mechanically to a temperature of 170-175° C. Sodium methyl isethionate solution in water (surfonic SMI, 1040 grams, 47%, 3.0 moles) was added slowly over 60-70 minutes at a rate that keeps the mixture completely liquid. Water was distilled over from the reaction mixture as surfonic SMI addition continued. After the addition of surfonic SMI was completed, the reaction mixture was heated slowly over 30-45 minutes to 225° C. and continued for 4 hours and then the excess fatty acid was stripped by dry nitrogen purge for 2-3 hours to lower fatty acid to a desired level, below 10%, preferably 6-8%. A sample was taken for acid value and was considered to be substantially complete if it was below 30. It was very important to keep air away from the hot reaction mixture to prevent color formation. The viscous and hot reaction product was poured into 2-liter beaker under nitrogen and allowed it to cool to room temp. A total 934 grams of waxy solid ester was obtained. Acid value of this ester was 26.06, i.e., 9.66% and ester's correct sap value of 128.65, i.e., 80.71% and estimated unreacted surfonic SMI was 9.50%.

Example 11

Preparation of Sodium Cocoyl ($C_8$-$C_{18}$) Methyl Isethionate Ester

In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stirred mechanically to a temperature of 170-175° C. Sodium methyl isethionate solution in water (surfonic SMI, 352.20 grams, 46%, 1.0 moles) was added slowly over 60-70 minutes at a rate that keeps the mixture completely liquid. Water was distilled over from the reaction mixture as surfonic SMI addition continued. After the addition of surfonic SMI was completed, the reaction mixture was heated slowly over 30-45 minutes to 225° C. and continued for 4 hours. The reaction mixture becomes completely homogeneous around 210-215° C. The excess fatty acid was stripped under vacuum at 175-200 mmHg over 1-2 hours with nitrogen leak into the system to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 341 grams of light yellow waxy solid ester was obtained. Acid value of this ester was 21.45, i.e., 7.95% and ester's correct sap value of 115.82, i.e., 72.66% and estimated unreacted surfonic SMI was 12.99%.

Example 12

Preparation of Sodium Cocoyl ($C_8$-$C_{18}$) Methyl Isethionate Ester (10 Mole % Excess Fatty Acid)

In a laboratory reactor (1000 ml round bottom flask equipped with a mechanical stirrer, an addition funnel, a condenser, a thermocouple, and gas sparging provision) 228.80 grams (1.10 moles) of a carboxylic acid (fatty acid Emery 626, Cognis, Cincinnati, Ohio) and 2.00 grams of zinc oxide (ZnO, 0.50 wt. %) were charged into the reactor, heated, and stirred mechanically to a temperature of 170-175° C. Sodium methyl isethionate solution in water (surfonic SMI, 352.20 grams, 46%, 1.0 moles) was added slowly over 60-70 minutes at a rate that keeps the mixture completely liquid. Water was distilled over from the reaction mixture as surfonic SMI addition continued. After the addition of surfonic SMI was completed, the reaction mixture was heated slowly over 30-45 minutes to 225° C. and continued for 4 hours. The reaction mixture becomes completely homogeneous around 210-215° C. The excess fatty acid was stripped by purging with nitrogen for 1-2 hours to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 340 grams of light yellow waxy solid ester was obtained. Acid value of this ester was 23.52, i.e., 8.72% and ester's correct sap value of 119.72, i.e., 75.11% and estimated unreacted surfonic SMI was 12.86%.

Example 13

Preparation of Sodium Cocoyl ($C_8$-$C_{18}$) Methyl Isethionate Ester (5 Mole % Excess Fatty Acid)

In a laboratory reactor (1000 ml round bottom flask equipped with a mechanical stirrer, an addition funnel, a condenser, a thermocouple, and gas sparging provision) 218.40 grams (1.05 moles) of a carboxylic acid (fatty acid Emery 626, Cognis, Cincinnati, Ohio) and 2.00 grams of zinc oxide (ZnO, 0.50 wt. %) were charged into the reactor, heated, and stirred mechanically to a temperature of 170-175° C. Sodium methyl isethionate solution in water (surfonic SMI, 352.20 grams, 46%, 1.0 moles) was added slowly over 60-70 minutes at a rate that keeps the mixture completely liquid. Water was distilled over from the reaction mixture as surfonic SMI addition continued. After the addition of surfonic SMI was completed, the reaction mixture was heated slowly over 30-45 minutes to 225° C. and continued for 4 hours. The reaction mixture becomes completely homogeneous around 210-215° C. The excess fatty acid was stripped by purging with nitrogen for 1-2 hours to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 356.20 grams of light yellow waxy solid ester was obtained. Acid value of this ester was 48.11, i.e., 17.84% and ester's correct sap value of 95.04, i.e., 59.62% and estimated unreacted surfonic SMI was 18.36%.

Example 14

Preparation of Sodium Cocoyl ($C_8$-$C_{18}$) Methyl Isethionate Ester (No Excess Fatty Acid)

In a laboratory reactor (1000 ml round bottom flask equipped with a mechanical stirrer, an addition funnel, a condenser, a thermocouple, and gas sparging provision) 208.0 grams (1.00 moles) of a carboxylic acid (fatty acid Emery 626, Cognis, Cincinnati, Ohio) and 1.90 grams of zinc oxide (ZnO, 0.50 wt. %) were charged into the reactor, heated, and stirred mechanically to a temperature of 170-175° C. Sodium methyl isethionate solution in water (surfonic SMI, 352.20 grams, 46%, 1.0 moles) was added slowly over 60-70 minutes at a rate that keeps the mixture completely liquid. Water was distilled over from the reaction mixture as surfonic SMI addition continued. After the addition of surfonic SMI was completed, the reaction mixture was heated slowly over 30-45 minutes to 225° C. and continued for 4 hours. The reaction mixture becomes completely homogeneous around 210-215° C. The excess fatty acid was stripped by purging with nitrogen for 1-2 hours to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 346.40 grams of light yellow waxy solid ester was obtained. Acid value of this ester was 34376, i.e., 12.74% and ester's correct sap value of 114.28, i.e., 71.69% and estimated unreacted surfonic SMI was 13.24%.

Example 15

Preparation of Sodium Oleyl Methyl Isethionate Ester

In a laboratory reactor (1000 ml round bottom flask equipped with a mechanical stirrer, an addition funnel, a condenser, a thermocouple, and gas sparging provision) 353 grams (1.25 moles) of oleic acid and 2.60 grams of zinc oxide (ZnO, 0.50 wt. %) were charged into the reactor, heated, and stirred mechanically to a temperature of 170-175° C. Sodium methyl isethionate solution in water (surfonic SMI, 352.20 grams, 46%, 1.0 moles) was added slowly over 60-70 minutes at a rate that keeps the mixture completely liquid. Water was distilled over from the reaction mixture as surfonic SMI addition continued. After the addition of surfonic SMI was completed, the reaction mixture was heated slowly over 30-45 minutes to 230° C. and continued for 6 hours. The reaction mixture becomes completely homogeneous around 215-220° C. The excess fatty acid was stripped with nitrogen sweep for 2-3 hours to lower the acid below 10%. It was very important to keep air away from the hot reaction mixture to prevent color formation. The viscous and hot reaction product was poured into a 1-liter beaker under nitrogen and allowed it to cool to room temp. A total 412 grams of yellow waxy solid ester was obtained. Acid value of this ester was 21.0, i.e., 10.57% and ester's correct sap value of 113.00, i.e., 69.94% and estimated unreacted surfonic SMI was 11.82%.

Example 16

Preparation of Sodium Cocoyl (C12-$C_{18}$) Methyl Isethionate Ester

In a laboratory reactor (1000 ml round bottom flask equipped with a mechanical stirrer, an addition funnel, a condenser, a thermocouple, and gas sparging provision) 275 grams (1.25 moles) of a carboxylic acid (fatty acid Emery 627, Cognis, Cincinnati, Ohio) and 4.40 grams of zinc oxide (ZnO, 1.00 wt. %) were charged into the reactor, heated, and stirred mechanically to a temperature of 170-175° C. Sodium methyl isethionate solution in water (surfonic SMI, 352.20 grams, 46%, 1.0 moles) was added slowly over 60-70 minutes at a rate that keeps the mixture completely liquid. Water was distilled over from the reaction mixture as surfonic SMI addition continued. After the addition of surfonic SMI was completed, the reaction mixture was heated slowly over 30-45 minutes to 220° C. and continued for 6 hours. The reaction mixture becomes completely homogeneous around 210-215° C. The excess fatty acid was stripped with nitrogen purge for 2-3 hours to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 361 grams of light yellow waxy solid ester was obtained. Acid value of this ester was 21.0, i.e., 8.24% and ester's correct sap value of 132.80, i.e., 86.18% and estimated unreacted surfonic SMI was 6.20%

Blend Preparations:

Example 17

Preparation of 9:1 Blend of Sodium Cocoyl ($C_8$-$C_{18}$) Methyl Isethionate (SCMI) and Sodium Cocoyl Isethionate (SCI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stirred mechanically to a temperature of 170-175° C. A blend of Sodium methyl isethionate solution in water (surfonic SMI, 317.00 grams, 46%, 0.90 moles) and sodium isethionate solution (surfonic SI, 38.00 grams, 57%, 0.10 moles) was added slowly over 60-70 minutes at a temperature of 175-180° C. and at a rate that keeps the mixture completely liquid. Water was distilled over from the reaction mixture as the blend of surfonic SMI/SI addition continued. After the addition of surfonic SMI/SI was completed, the reaction mixture was heated slowly over 30-45 minutes to 225° C. and continued for 4 hours. The reaction mixture becomes completely homogeneous around 210-215° C. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 362 grams of almost colorless soft solid ester was obtained. Acid value of this ester was 16.96, i.e., 6.29% and ester's correct sap value of 134.43, i.e., 84.01% and estimated unreacted surfonic SMI+SI was 7.16%

Example 18

Preparation of 8:2 Blend of Sodium Cocoyl ($C_8$-$C_{18}$) Methyl Isethionate (SCMI) and Sodium Cocoyl Isethionate (SCI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stirred mechanically to a temperature of 170-175° C. A blend of Sodium methyl isethionate solution in water (surfonic SMI, 282.00 grams, 46%, 0.80 moles) and sodium isethionate solution (surfonic SI, 52.00 grams, 57%, 0.20 moles) was added slowly over 60-70 minutes at a temperature of 120-130° C. and at a rate that keeps the mixture completely liquid. Water was distilled over from the reaction mixture as the blend of surfonic SMI/SI addition continued. After the addition of surfonic SMI/SI was completed, the reaction mixture was heated slowly over 30-45 minutes to 225° C. and continued for 4 hours. The reaction mixture becomes completely homogeneous around 210-215° C. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 362 grams of almost colorless soft solid ester was obtained. Acid value of this ester was 23.51, i.e., 8.72% and ester's correct sap value of 131.71, i.e., 81.99% and estimated unreacted surfonic SMI+SI was 8.06%

Example 19

Preparation of 7:3 Blend of Sodium Cocoyl ($C_8$-$C_{18}$) Methyl Isethionate (SCMI) and Sodium Cocoyl Isethionate (SCI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stirred mechanically to a temperature of 150-155° C. A blend of Sodium methyl isethionate solution in water (surfonic SMI, 247.00 grams, 46%, 0.70 moles) and sodium isethionate solution (surfonic SI, 78.00 grams, 57%, 0.30 moles) was added slowly over 60-70 minutes at a temperature of 125-145° C. and at a rate that keeps the mixture completely liquid. Water was distilled over from the reaction mixture as the blend of surfonic SMI/SI addition continued. After the addition of surfonic SMI/SI was completed, the reaction mixture was heated slowly over 30-45 minutes to 225° C. and continued for 4 hours. The reaction mixture becomes completely homogeneous around 170-175° C. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 355 grams of almost colorless soft solid ester was obtained. Acid value of this ester was 20.53, i.e., 7.61% and ester's correct sap value of 147.69, i.e., 91.56% and estimated unreacted surfonic SMI+SI was 3.85%.

Example 20

Preparation of 6:4 Blend of Sodium Cocoyl ($C_8$-$C_{18}$) Methyl Isethionate (SCMI) and Sodium Cocoyl Isethionate (SCI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stirred mechanically to a temperature of 140-145° C. A blend of Sodium methyl isethionate solution in water (surfonic SMI, 211.30 grams, 46%, 0.60 moles) and sodium isethionate solution (surfonic SI, 103.80 grams, 57%, 0.40 moles) was added slowly over 40-50 minutes, at a temperature of 130-150° C. at a rate that keeps the mixture completely liquid. Water was distilled over from the reaction mixture as the blend of surfonic SMI/SI addition continued. After the addition of surfonic SMI/SI was completed. The reaction mixture becomes completely homogeneous around 160-165° C. The reaction mixture was heated slowly over 30-45 minutes to 225° C. and continued for 4 hours. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 360.30 grams of almost colorless solid ester was obtained. Acid value of this ester was 21.25, i.e., 7.881% and ester's correct sap value of 139.23, i.e., 85.97% and estimated unreacted surfonic SMI+SI was 6.31%.

Example 21

Preparation of 5:5 Blend of Sodium Cocoyl ($C_8$-$C_{18}$) Methyl Isethionate (SCMI) and Sodium Cocoyl Isethionate (SCI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stirred mechanically to a temperature of 140-145° C. A blend of Sodium methyl isethionate solution in water (surfonic SMI, 176.0 grams, 46%, 0.50 moles) and sodium isethionate solution (surfonic SI, 130.0 grams, 57%, 0.50 moles) was added slowly over 40-50 minutes at a temperature of 132-160° C. and at a rate that keeps the mixture completely liquid. Water was distilled over from the reaction mixture as the blend of surfonic SMI/SI addition continued. After the addition of surfonic SMI/SI was completed. The reaction mixture becomes completely homogeneous around 160-165° C. The reaction mixture was heated slowly over 30-45 minutes to 225° C. and continued for 4 hours. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 363.50 grams of almost colorless solid ester was obtained. Acid value of this ester was 22.78, i.e., 8.45% and ester's correct sap value of 133.39, i.e., 82.03% and estimated unreacted surfonic SMI+SI was 8.0%.

Example 22

Preparation of 4:6 Blend of Sodium Cocoyl ($C_8$-$C_{18}$) Methyl Isethionate (SCMI) and Sodium Cocoyl Isethionate (SCI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stirred mechanically to a temperature of 140-145° C. A blend of Sodium methyl isethionate solution in water (surfonic SMI, 140.87 grams, 46%, 0.40 moles) and sodium isethionate solution (surfonic SI, 155.70 grams, 57%, 0.60 moles) was added slowly over 40-45 at a temperature of 140-157° C. and minutes at a rate that keeps the mixture completely liquid. Water was distilled over from the reaction mixture as the blend of surfonic SMI/SI addition continued. After the addition of surfonic SMI/SI was completed. The reaction mixture becomes completely homogeneous around 160-165° C. The reaction mixture was heated slowly over 30-45 minutes to 225° C. and continued for 4 hours. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 364 grams of almost colorless solid ester was obtained. Acid value of this ester was 22.69, i.e., 8.41% and ester's correct sap value of 140.90, i.e., 86.30% and estimated unreacted surfonic SMI+SI was 6.05%

Example 23

Preparation of 3:7 Blend of Sodium Cocoyl ($C_8$-$C_{18}$) Methyl Isethionate (SCMI) and Sodium Cocoyl Isethionate (SCI) Esters In a laboratory reactor (1000 ml round bottom flask equipped with a mechanical stirrer, an addition funnel, a condenser, a thermocouple, and gas sparging provision) 260 grains (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stirred mechanically to a temperature of 145-155° C. A blend of Sodium methyl isethionate solution in water (surfonic SMI, 105.65 grams, 46%, 0.30 moles) and sodium isethionate solution (surfonic SI, 181.75 grams, 57%, 0.70 moles) was added slowly over 40-45 minutes at a temperature of 150-165° C. and at a rate that keeps the mixture completely liquid. Water was distilled over from the reaction mixture as the blend of surfonic SMI/SI addition continued. After the addition of surfonic SMI/SI was completed. The reaction mixture becomes completely homogeneous around 160-165° C. The reaction mixture was heated slowly over 30-45 minutes to 225° C. and continued for 4 hours. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 370 grams of almost colorless solid ester was obtained. Acid value of this ester was 22.75, i.e., 8.43% and ester's correct sap value of 136.37, i.e., 83.18% and estimated unreacted surfonic SMI+SI was 7.40%.

Example 24

Preparation of 2:8 Blend of Sodium Cocoyl ($C_8$-$C_{18}$) Methyl Isethionate (SCMI) and Sodium Cocoyl Isethionate (SCI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stiffed mechanically to a temperature of 155-165° C. A blend of Sodium methyl isethionate solution in water (surfonic SMI, 70.40 grams, 46%, 0.20 moles) and sodium isethionate solution (surfonic SI, 207.72 grams, 57%, 0.80 moles) was added slowly over 40-45 minutes at a temperature of 130-177° C. and at a rate that keeps the mixture completely liquid. Water was distilled over from the reaction mixture as the blend of surfonic SMI/SI addition continued. After the addition of surfonic SMI/SI was completed. The reaction mixture becomes completely homogeneous around 170-175° C. The reaction mixture was heated slowly over 30-45 minutes to 225° C. and continued for 4 hours. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 369 grams of almost colorless solid ester was obtained. Acid value of this ester was 28.89, i.e., 10.71% and ester's correct sap value of 132.67, i.e., 80.60% and estimated unreacted surfonic SMI+SI was 8.52%.

Example 25

Preparation of 1:9 Blend of Sodium Cocoyl ($C_8$-$C_{18}$) Methyl Isethionate (SCMI) and Sodium Cocoyl Isethionate (SCI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 2.10 grams of zinc oxide (ZnO, 0.50 wt. %) were charged into the reactor, heated, and stirred mechanically to a temperature of 155-165° C. A blend of Sodium methyl isethionate solution in water (surfonic SMI, 35.20 grams, 46%, 0.10 moles) and sodium isethionate solution (surfonic SI, 233.70 grams, 57%, 0.90 moles) was added slowly over 40-45 minutes at a temperature of 130-150° C. and at a rate that keeps the mixture completely liquid. Water was distilled over from the reaction mixture as the blend of surfonic SMI/SI addition continued. After the addition of surfonic SMI/SI was completed. The reaction mixture becomes completely homogeneous around 170-175° C. The reaction mixture was heated slowly over 30-45 minutes to 225-240° C. and continued for 4 hours. The temperature has gradually increased with time to make it less viscous because of SCI which was considerably higher melting. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 348 grams of almost colorless solid ester was obtained. Acid value of this ester was 16.50, i.e., 6.12% and ester's correct sap value of 138.14, i.e., 83.57% and estimated unreacted surfonic SMI+SI was 7.65%.

Example 26

Preparation of 9:1 Blend of Sodium Cocoyl ($C_8$-$C_{18}$) Methyl Isethionate (SCMI) and Sodium Cocoyl Ethyl Isethionate (SCEI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 1.00 grams of zinc oxide (ZnO, 0.25 wt. %) were charged into the reactor, heated, and stirred mechanically to a temperature of 170-175° C. A blend of Sodium methyl isethionate solution in water (surfonic SMI, 317.00 grams, 46%, 0.90 moles) and sodium ethyl isethionate (surfonic SEI, 17.60 grams, solid, 0.10 moles) was added slowly over 60-70 minutes at a temperature of 125-136° C. and at a rate that keeps the mixture completely liquid. Water was distilled over from the reaction mixture as the blend of surfonic SMI/SEI addition continued. After the addition of surfonic SMI/SEI was completed, the reaction mixture was heated slowly over 30-45 minutes to 225° C. and continued for 4 hours. The reaction mixture becomes completely homogeneous around 210-215° C. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 356.80 grams of almost colorless soft solid ester was obtained. Acid value of this ester was 36.80, i.e., 13.64% and Active ester component value 73.37% and estimated unreacted surfonic SMI+SEI was 12.15%

Example 27

Preparation of 9:1 Blend of Sodium Cocoyl ($C_8$-$C_{18}$) Isethionate (SCMI) and Sodium Cocoyl Ethyl Isethionate (SCEI) Esters In a laboratory reactor (1000 ml round bottom flask equipped with a mechanical stirrer, an addition funnel, a condenser, a thermocouple, and gas sparging provision) 260 grams (1.25 moles) of a carboxylic acid (fatty acid Emery 626, Cognis, Cincinnati, Ohio) and 1.00 grams of zinc oxide (ZnO, 0.25 wt. %) were charged into the reactor, heated, and stirred mechanically to a temperature of 170-175° C. A blend of Sodium isethionate solution in water (surfonic SI, 233.68 grams, 57%, 0.90 moles) and sodium ethyl isethionate solution (surfonic SEI, 17.60 grams, solid, 0.10 moles) was added slowly over 60-70 minutes at a rate that keeps the mixture completely liquid. Water was distilled over from the reaction mixture as the blend of surfonic SI/SEI addition continued. After the addition of surfonic SI/SEI was completed, the reaction mixture was heated slowly over 30-45 minutes to 225-230° C. and continued for 4 hours. The excess fatty acid was stripped with nitrogen purge over 1-2 hours with to a desired fatty acid level, below 10%, preferably 6-8%. It was very important to keep air away from the hot reaction mixture to prevent color formation. The viscous and hot reaction product was poured into a 1-liter beaker under nitrogen and allowed it to cool to room temp. A total 348.0 grams of almost colorless solid ester was obtained. Acid value of this ester was 15.43, i.e., 5.72% and Active ester component value 83.87% and estimated unreacted surfonic SI+SEI was 6.99%.

Example 28

Foaming Tests

Foaming tests were performed using a one-liter capped rotating measuring cylinder foam machine at a rate of 30 revolutions per minute and ambient temperature ranging from about 20° C. to about 22° C. and at a concentration of 0.5% of total surfactants. Foam heights in the graduated cylinder were measured at the start and at 10 minutes of rotation. The results are shown below in Table I:

TABLE I

| Sample | Ingredients (% By Weight) | Foam Height at 0 minutes, ml | Foam Height at 10 minutes, ml | Foam Appearance |
|---|---|---|---|---|
| 1 | 80% sodium lauryl sulfate 20% CAPB* | 250 | 238 | Open Foam |

TABLE I-continued

| Sample | Ingredients (% By Weight) | Foam Height at 0 minutes, ml | Foam Height at 10 minutes, ml | Foam Appearance |
|---|---|---|---|---|
| 2 | 100% sodium laureth sulfate** | 200 | 170 | Open Foam |
| 3 | 80% sodium laureth sulfate 20% CAPB* | 260 | 220 | Open Foam |
| 4 | 100% SCMI*** | 190 | 160 | Creamy, Tight |
| 5 | 80% SCMI*** 20% CAPB* | 190 | 180 | Creamy, Tight |

*Cocoamidopropyl Betaine (EMPIGEN ® BS/FA)
**EMPICOL ® ESA
***SCMI produced from $C_8$ to $C_{18}$ whole coco fatty acid Sample 1 was a commercial product example having one of the highest flash foam levels in the personal care industry and was used as an internal standard throughout these tests.

The results of this foam test show that the foaming of the $C_8$ to $C_{18}$ SCMI alone was not quite as good as SLES alone, but it still shows synergy with CAPB betaine. This synergy was similar to other anionic surfactants as shown by the results for Sample 5 when 20% by weight SCMI was replaced with CAPB. Thus, SCMI can be used with other surfactants and still maintain excellent foaming properties. The SCMI also shows a consistently tighter, creamier foam as it has smaller bubble size than SLES in these types of formulations.

A second foaming test was performed using the same parameters as above, but a stripped coco fatty acid chain SCMI was tested in place of a whole coco fatty acid chain SCMI. The results of this test are shown in Table II:

TABLE II

| Sample | Ingredients (% By Weight) | Foam Height at 0 minutes, ml | Foam Height at 10 minutes, ml | Foam Appearance |
|---|---|---|---|---|
| 1 | 80% sodium lauryl sulfate 20% CAPB* | 250 | 235 | Open Foam |
| 2 | 100% sodium lauryl sulfate | 255 | 245 | Open Foam |
| 3 | 100% SCMI** | 205 | 205 | Creamy, tight |
| 4 | 75% SCMI** 25% CAPB* | 220 | 215 | Creamy, Tight |
| 5 | 82% SCMI*** 18% CAPB* | 230 | 230 | Creamy, Tight |

*Cocoamidopropyl Betaine (EMPIGEN ® BS/FA)
**SCMI produced from $C_{12}$ to $C_{18}$ stripped coco fatty acid Again, the results of this foam test show that foaming can be significantly increased when using a stripped coco fatty acid feed SCMI instead of whole coco fatty acid. The $C_{12}$ to $C_{18}$ SCMI flash foam height, as well as the stability at 10 minutes, were better than SLES alone and were similar to SLES/betaine performance. Furthermore, the $C_{12}$ to $C_{18}$ SCMI was again synergistic with CAPB as shown by the results for Samples 4 and 5 when 25% and 18% by weight of SCMI was replaced with CAPB. Thus, SCMI can be used with other surfactants and still maintain or improve excellent foaming properties.

Figure 1B:
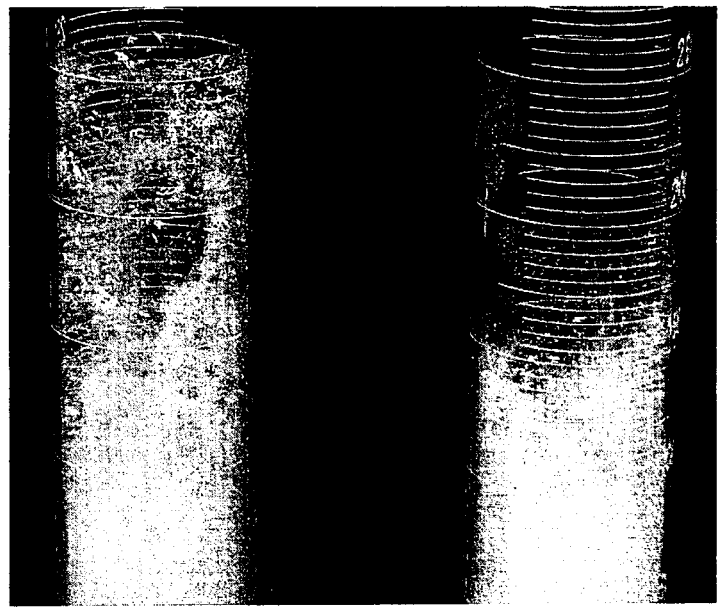
FIG. 1B depicts the foaming characteristics of sodium lauryl ether sulfate (SLES) and sodium lauryl sulfate (SLS).

Finally, as shown in FIGS. 1A and 1B, the foam appearance of SCMI was tighter and creamier than SLES or SLS based cleansers making the use of SCMI in personal care cleansers highly desirable. All samples shown in FIGS. 1A and 1B were at 0.5% active of surfactant.

Example 29

Zein Irritation Score

To evaluate the mildness of the products of the present invention, Zein scores were determined for a variety of sulfate and isethionate surfactants and their scores are reported in Table III:

TABLE III

| Product | Zein Score (mg N/100 ml solution) |
|---|---|
| Sodium Lauryl Sulfate | 527 |
| Sodium Cocoyl Isethionate | 254 |
| Sodium Cocoyl Methyl Isethionate | 147 |
| Sodium Cocoyl Ethyl Isethionate | 104 |
| Sodium Lauroyl Isethionate | 160 |
| Sodium Lauroyl Methyl Isethionate | 134 |
| Sodium Lauroyl Ethyl Isethionate | 187 |

From these in vitro results, the methyl and ethyl isethionates of the present invention were expected to be less irritating and therefore milder than sodium cocoyl isethionate which has been noted in the literature to be a non-skin irritant and eye irritant at levels of 10% by weight. The lower the Zein score, the more mild the composition.

Example 30

Use of Sodium Cocoyl Methyl Isethionate as a Primary Surfactant in High Foaming Personal Cleansers An SCMI Concentrate can be produced by directly adding the molten SCMI produced, such as in Example 3, into a solution of water and betaines (e.g. EMPIGEN® BS/FA, Huntsman Corporation, The Woodlands, Tex.). If the SCMI was in a powder or flaked form, the SCMI Concentrate may be formed by dissolving the SCMI powder or flakes in a solution containing cold water and betaines.

The SCMI Concentrate that was formed was a white pearlescent solution having a viscosity ranging from 3000-5000 cps. The SCMI Concentrate was easy to handle and its physical properties were similar to sodium laureth sulfate (e.g. EMPICOL®, Huntsman Corporation, The Woodlands, Tex.) allowing for its use in existing manufacturing facilities without the need for equipment upgrades.

As shown in Table IV, the SCMI Concentrate can be formulated as follows:

TABLE IV

SCMI Concentrate Formulation

| Ingredient | Amount (% By Weight) |
|---|---|
| SCMI | 24.0 |
| CAPB* | 17.0 |
| DMDM Hydantoin | 0.4 |
| Water | q.s. to 100.0 |

*EMPIGEN ® BS/FA

The SCMI Concentrate can be used in the formulation of a variety of personal care cleansers as shown in Tables V to XI.

TABLE V

Simple Economic Shampoo Formulation

| Ingredient | Amount (% By Weight) |
| --- | --- |
| SCMI | 8.0 |
| CAPB* | 2.0 |
| Sodium laureth sulfate** | 1.8 |
| DMDM Hydantoin 55% | 0.4 |
| Water | q.s. to 100.0 |

*EMPIGEN ® BS/FA
**EMPICOL ® ESB

TABLE VI

Low Irritation Shampoo Formulation

| Ingredient | Amount (% By Weight) |
| --- | --- |
| SCMI | 5.0 |
| Disodium Lauroamphoacetate* | 2.8 |
| Polysorbate 80 | 4.9 |
| DMDM Hydantoin 55% | 0.4 |
| Water | q.s. to 100.0 |

*EMPIGEN ® CDL60P

TABLE VII

Baby Shampoo Formulation

| Ingredient | Amount (% By Weight) |
| --- | --- |
| SCMI | 4.0 |
| Disodium Lauroamphoacetate* | 3.0 |
| Polysorbate 80 | 5.9 |
| DMDM Hydantoin 55% | 0.4 |
| Water | q.s. to 100.0 |

*EMPIGEN ® CDL60P

TABLE VIII

Luxurious Liquid Soap Formulation

| Ingredient | Amount (% By Weight) |
| --- | --- |
| SCMI | 6.7 |
| Disodium Lauroamphoacetate* | 2.5 |
| CAPB** | 2.5 |
| DMDM Hydantoin 55% | 0.4 |
| Water | q.s. to 100.0 |

*EMPIGEN ® CDL60P
**EMPIGEN ® BS/FA

TABLE IX

Economic Liquid Soap Formulation

| Ingredient | Amount (% By Weight) |
| --- | --- |
| SCMI | 4.9 |
| Disodium Lauroamphoacetate* | 3.0 |
| CAPB** | 2.2 |
| DMDM Hydantoin** | 0.4 |
| Water | q.s. to 100.0 |

*EMPIGEN ® NHSSA
**EMPIGEN ® BS/FA

TABLE X

Shower gel Formulation

| Ingredient | Amount (% By Weight) |
| --- | --- |
| SCMI | 10.2 |
| Sodium laureth sulfate* | 3.9 |
| CAPB** | 2.5 |
| DMDM Hydantoin 55% | 0.4 |
| Water | q.s. to 100.0 |

*EMPICOL ® ESB70
**EMPIGEN ® BS/FA

TABLE XI

Concentrated Shower gel Formulation

| Ingredient | Amount (% By Weight) |
| --- | --- |
| SCMI | 12.0 |
| Sodium laureth sulfate* | 4.0 |
| CAPB** | 2.5 |
| DMDM Hydantoin 55% | 0.4 |
| Water | q.s. to 100.0 |

*EMPICOL ® ESB70
**EMPIGEN ® BS/FA

All formulations produced above using SCMI as the primary surfactant form a clear solution that was hydrolytically stable when stored. In comparison, when SCMI was replaced with SCI as the primary surfactant, the formulations were cloudy and separate when stored. Therefore, the use of SCMI as a primary surfactant in personal care cleansers was desirable since it was highly soluble, hydrolytically stable and milder to the skin.

Example 31

To determine the solubility in combination with taurates of SCI, SCMI and SCEI, three solutions were prepared at ambient temperature. The solutions were formulated to each contain one of SCI, SCMI and SCEI and each contained the following ingredients as shown in Table XII:

TABLE XII

Solubility in Taurate

| Ingredient | Solution 1 (% By Weight) | Solution 2 (% By Weight) | Solution 3 (% By Weight) |
| --- | --- | --- | --- |
| SCI | 12.5 | 0 | 0 |
| SCMI | 0 | 12.5 | 0 |
| SCEI | 0 | 0 | 12.5 |
| Disodium Lauroamphoacetate* | 3.7 | 3.7 | 3.7 |
| Sodium Methyl Cocoyl Taurate | 9 | 9 | 9 |
| Sodium Xylene Sulfonate | 0.8 | 0.8 | 0.8 |
| Propylene Glycol | 1.9 | 1.9 | 1.9 |
| DMDM Hydantoin 55% | 0.22 | 0.22 | 0.22 |
| Water | q.s. to 100.0 | q.s. to 100.0 | q.s. to 100.0 |

*EMPIGEN ® CDL60P

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. The present disclosure includes the subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claim so modified. This also includes combination of the features and/or limitations of one or more of the independent claims with the features and/or limitations of another independent claim to arrive at a modified independent claim, with the remaining dependent claims in their original text being read and applied to any independent claim so modified. Accordingly, the presently disclosed invention was intended to cover all such modifications and alterations, and was limited only by the scope of the claims which follow, in view of the foregoing and other contents of this specification. Throughout this specification, various percentages have been set forth and these percentages all refer to percent by weight, unless set forth to the contrary.

Blend Solubility Experiments:

Surfonic SCMI has demonstrated its ability to enhance the solubility of SCI and AGS-1214 in formulations which couldn't have been possible otherwise. SCMI could be used as primary and/or secondary surfactant to enhance the performance and reduce the skin irritation levels. The formulations below demonstrate these but not limited to them only. The following are example formulations having SCMI, SCI, and AGS-1214P mixtures.

Example 32

A reduced irritation formulation using SCMI and SLS was prepared as follows. The following components were added:

| Ingredient | Amount (% by weight) |
| --- | --- |
| SCMI Solution (30% solids) | 30.50 |
| SLS Solids | 2.00 |
| CapB (35% solids) | 2.50 |
| KCl Solid | 1.00 |
| Water and Preservative | qs to 100, | and then all of the components were weighed into a beaker and warmed up to 50-55° C. to dissolve all solids and cooled to about 30° C. Solid KCl was added and mixed well to desired viscosity and then added desired preservative. The clear viscous liquid had a viscosity of 2760° Cps@ 30 rpm. Spindle #3 and had a pH of 6.30

Example 33

A reduced irritation formulation using SCMI and AGS-1214P was prepared as follows. The following components were added:

| Ingredient | Amount (% by weight) |
| --- | --- |
| SCMI solution (30% solids) | 30.50 |
| AGS-1214P (57% solids) | 9.00 |
| CapB (35% solids) | 2.50 |
| Cocoamide MEA | 2.00 |
| KCl solid | 1.00 |
| Water and preservative | Qs to 100, | and then all of the components were weighed into a beaker and warmed up to 50-55° C. to dissolve all solids and cooled to about 30° C. Solid KCl was added and mixed well to desired viscosity and then added desired preservative. The clear viscous liquid had a viscosity of 17972 cps@ 5 rpm. Spindle #3 and had a pH of 6.30

Example 34

A reduced irritation formulation using SCMI and SCI was prepared as follows. The following components were added:

| Ingredient | Amount (% by weight) |
| --- | --- |
| SCMI solution (30% solids) | 30.00 |
| SCI (solid) | 5.00 |
| CapB (35% solids) | 2.00 |
| Cocoamide MEA | 2.00 |
| KCl solid | 0.50 |
| Water and preservative | Qs to 100, | and then all of the components were weighed into a beaker and warmed up to 50-55° C. to dissolve all solids and cooled to about 30° C. Solid KCl was added and mixed well to desired viscosity and then added desired preservative. The clear viscous liquid had a viscosity of 5273 cps@ 5 rpm. Spindle #3 and had a pH of 6.50

Example 35

A reduced irritation formulation using SCMI, SLS and Gello Gelatin was prepared as follows. The following components were added:

| Ingredient | Amount (% by weight) |
| --- | --- |
| SCMI solution (30% solids) | 40.00 |
| SLS (solids) | 2.00 |
| CapB (35% solids) | 2.00 |
| Cocoamide MEA | 2.00 |
| KCl solid | 1.00 |
| 1% gello gelatin Water and preservative | Qs to 100, | and then all of the components were weighed into a beaker and warmed up to 50-55° C. to dissolve all solids and cooled to about 30° C. Solid KCl was added and mixed well to desired viscosity and then added desired preservative. The clear viscous liquid had a viscosity of 3363 cps@ 30 rpm. Spindle #3 and had a pH of 6.30

Example 36

A reduced irritation formulation using SCMI, AGS-1214P and Gello Gelatin was prepared as follows. The following components were added:

| Ingredient | Amount (% by weight) |
| --- | --- |
| SCMI solution (30% solids) | 30.00 |
| AGS-1214P (57% solids) | 5.00 |
| CapB (35% solids) | 2.00 |
| Cocoamide MEA | 2.00 |
| KCl solid | 0.25 |
| 2% gellogelatin Water and preservative | Qs to 100, | and then all of the components were weighed into a beaker and warmed up to 50-55° C. to dissolve all solids and cooled to about 30° C. Solid KCl was added and mixed well to desired viscosity and then added desired preservative. The clear viscous liquid had a viscosity of 1408 cps@ 30 rpm. Spindle #3 and had a pH of 6.30

Example 37

A reduced irritation formulation using SCMI and SCI was prepared as follows. The following components were added:

| Ingredient | Amount (% by weight) |
| --- | --- |
| SCMI solution (30% solids) | 25.00 |
| SCI (solids, 85% ester) | 4.70 |
| CapB (35% solids) | 2.00 |
| Cocoamide MEA | 2.00 |
| KCl solid | 1.00 |
| Water and preservative | qs to 100, | and then all of the components were weighed into a beaker and warmed up to 50-55° C. to dissolve all solids and cooled to about 30° C. Solid KCl was added and mixed well to desired viscosity and then added desired preservative. The clear viscous liquid had a viscosity of 880° Cps@ 30 rpm. Spindle #3 and had a pH of 6.50

Example 38

A reduced irritation formulation using SCMI, SLS and Gello Gelatin was prepared as follows. The following components were added:

| Ingredient | Amount (% by weight) |
| --- | --- |
| SCMI solution (30% solids) | 25.00 |
| AGS-1214P (57% solids) | 10.00 |
| CapB (35% solids) | 2.00 |
| Cocoamide MEA | 2.00 |
| KCl solid | 0.50 |
| 1% gellogelatin Water and preservative | Qs to 100, | and then all of the components were weighed into a beaker and warmed up to 50-55° C. to dissolve all solids and cooled to about 30° C., Solid KCl was added and mixed well to desired viscosity and then added desired preservative. The clear viscous liquid had a viscosity of 1600° Cps@ 30 rpm. Spindle #3 and had a pH of 7.00.

Example 39

A reduced irritation formulation using SCMI, SCI, and AGS-1214P was prepared as follows. The following components were added;

| Ingredient | Amount (% by weight) |
| --- | --- |
| SCMI (30% solids) | 25.00 |
| SCI solid (85% ester) | 3.00 |
| AGS-1214P (57% solids) | 5.00 |
| CapB (35% solids) | 2.00 |
| Cocamide MEA | 2.00 |
| KCl (solid) | 1.00 |
| Water and preservative | Qs to 100, | and then all of the components were weighed into a beaker and warmed up to 50-55° C. to dissolve all solids and cooled to about 30° C. Solid KCl was added and mixed well to desired viscosity and then added desired preservative. The clear viscous liquid had a viscosity of 10582 cps@ 10 rpm. Spindle #3 and had a pH of 6.50

Example 40

A reduced irritation formulation using SCMI, SLES and Kelzan ST was prepared as follows. The following components were added:

| Ingredient | Amount (% by weight) |
| --- | --- |
| SCMI solution (30% solids) | 30.00 |
| SLES (70% solids) | 2.00 |
| CapB (35% solids) | 2.00 |
| Cocoamide MEA | 2.00 |
| KCl solid | 0.00 |
| 2% Kelzan ST in Water and preservative | Qs to 100, | and then all of the components were weighed into a beaker and warmed up to 50-55° C. to dissolve all solids and cooled to about 30° C. and measured viscosity and then added desired preservative. This not so clear viscous liquid had a viscosity of 1770° Cps@ 20 rpm. Spindle #3 and had a pH of 7.10.

Example 41

A reduced irritation formulation using SCMI and SLS was prepared as follows. The following components were added:

| Ingredient | Amount (% by weight) |
| --- | --- |
| SCMI solution (30% solids) | 25.00 |
| SLS (70% solids) | 4.00 |
| CapB (35% solids) | 2.00 |
| Cocoamide MEA | 2.00 |
| KCl solid | 1.00 |
| Water and preservative | Qs to 100, | and then all of the components were weighed into a beaker and warmed up to 50-55° C. to dissolve all solids and cooled to about 30° C. KCl was added, mixed well and measured viscosity and then added desired preservative. This clear viscous liquid had a viscosity of 1374 cps@ 60 rpm. Spindle #3 and had a pH of 6.50.

Example 42

A reduced irritation formulation using SCMI and AGS-1214P was prepared as follows. The following components were added:

| Ingredient | Amount (% by weight) |
| --- | --- |
| SCMI solution (10% solids) | 30.00 |
| AGS-1214P (57% solids) | 6.00 |
| CapB (35% solids) | 1.00 |
| Cocoamide MEA | 1.00 |
| KCl solid | 1.25 |
| Water and preservative | qs to 100, | and then all of the components were weighed into a beaker and warmed up to 50-55° C. to dissolve all solids and cooled to about 30° C. and measured viscosity and then added desired preservative. This clear viscous liquid had a viscosity of 2238 cps@ 10 rpm. Spindle #3 and had a pH of 6.50.

Example 43

A reduced irritation formulation using SCMI and SOMI was prepared as follows. The following components were added:

| Ingredient | Amount (% by weight) |
| --- | --- |
| SCMI solution (10% solids) | 71.00 |
| SOMI (sodium oleyl methylisethionate, 10% solids) | 25.00 |
| CapB (35% solids) | 2.00 |
| Cocoamide MEA | 2.00 |
| KCl solid | 0.25 |
| Water and preservative | qs to 100, | and then all of the components were weighed into a beaker and warmed up to 50-55° C. to dissolve all solids and cooled to about 30° C., and measured viscosity and then added desired preservative. This clear viscous gel like material had a viscosity of 3539 cps@ 20 rpm. Spindle #3 and had a pH of 6.50.

Example 44

A reduced irritation formulation using SCMI/SCI blend and SCI was prepared as follows. The following components were added:

| Ingredient | Amount (% by weight) |
| --- | --- |
| SCMI + SCI (9:1) solid (84.0% active) | 5.00 |
| Empigen BR (A&W, 35%)) | 10.00 |
| Empigen CDR-60 (A&W, 35%) | 5.00 |
| Empicol SDD/UEF (35%) | 3.00 |
| Glycereth 26 | 3.00 |
| Water and preservative | qs to 100, | and then all of the components were weighed into a beaker and warmed up to 50-55° C. to dissolve all solids and cooled to about 30° C. and measured viscosity and then added desired preservative. This clear viscous material had a viscosity of 433 cps@ 100 rpm. Spindle #3 and had a pH of 7.47 and adjusted to 5.60 with 20% citric acid solution. It remained clear at 7 C for three days.

Example 45

A reduced irritation formulation using SCMI/SCI blend, SLES and Kelzan ST was prepared as follows. The following components were added:

| Ingredient | Amount (% by weight) |
| --- | --- |
| SCMI + SCI (8:2) solid (82.0% active) | 5.10 |
| Empigen BR (A&W, 35%)) | 12.00 |
| Empigen CDR-60 (A&W, 35%) | 3.00 |
| Empicol SDD/UEF (35%) | 3.00 |
| Glycereth 26 | 3.00 |
| Water and preservative | qs to 100, | and then all of the components were weighed into a beaker and warmed up to 50-55° C. to dissolve all solids and cooled to about 30° C. and measured viscosity and then added desired preservative. This clear viscous material had a viscosity of 365° Cps@ 100 rpm. Spindle #3 and had a pH of 6.64 and was lowered with 20% citric acid to 5.58. It remained clear at 7 C for three days.

Example 46

A reduced irritation formulation using SCMI/SCI blend, SLES and Kelzan ST was prepared as follows. The following components were added:

| Ingredient | Amount (% by weight) |
| --- | --- |
| SCMI + SCI (7:3) solid (89.0% active) | 5.00 |
| Empigen BR (A&W, 35%)) | 10.00 |
| Empigen CDR-60 (A&W, 35%) | 5.00 |
| Empicol SDD/UEF (35%) | 3.00 |
| Glycereth 26 | 3.00 |
| Water and preservative | qs to 100, | and then all of the components were weighed into a beaker and warmed up to 50-55° C. to dissolve all solids and cooled to about 30° C. and measured viscosity and then added desired preservative. This clear viscous material had a viscosity of 202 cps@ 100 rpm. Spindle #3 and had a pH of 7.41 and was lowered with 20% citric acid to 5.60. Viscosity was increased with 0.50 g of KCl to 2819 cps@20 rpm. It remained clear at 7 C for three days.

Example 47

A reduced irritation formulation using SCMI/SCI blend, SLES and Kelzan ST was prepared as follows. The following components were added:

| Ingredient | Amount (% by weight) |
| --- | --- |
| SCMI + SCI (6:4) solid (86.0% active) | 5.00 |
| Empigen BR (A&W, 35%)) | 10.00 |
| Empigen CDR-60 (A&W, 35%) | 5.00 |
| Empicol SDD/UEF (35%) | 3.00 |
| Glycereth 26 | 3.00 |
| KCl solid | 0.60 |
| Water and preservative | qs to 100, | and then all of the components were weighed into a beaker and warmed up to 50-55° C. to dissolve all solids and cooled to about 30° C. and measured viscosity and then added desired preservative. This clear viscous material had a viscosity of 136 cps@ 100 rpm. Spindle #3 and had a pH of 7.40 and was lowered with 20% citric acid to 5.64. Viscosity was increased with KCl to 1782 cps@20 rpm. It remained clear at 7 C for three days. No phase separation even after four freeze and thaw cycles.

Example 48

A reduced irritation formulation using SCMI/SCI blend, SLES and Kelzan ST was prepared as follows. The following components were added:

| Ingredient | Amount (% by weight) |
| --- | --- |
| SCMI + SCI (5:5) solid (82.0% active) | 5.00 |
| Empigen BR (A&W, 35%)) | 10.00 |
| Empigen CDR-60 (A&W, 35%) | 5.00 |
| Empicol SDD/UEF (35%) | 3.00 |
| Glycereth 26 | 3.00 |
| KCl solid | 0.50 |
| Water and preservative | qs to 100, | and then all of the components were weighed into a beaker and warmed up to 50-55° C. to dissolve all solids and cooled to about 30° C. and measured viscosity and then added desired preservative. This clear viscous material had a viscosity of 305° Cps@ 100 rpm. Spindle #3 and had a pH of 7.32 and was lowered with 20% citric acid to 5.56. Viscosity was increased with KCl to 1674 cps@20 rpm. It remained clear at 7 C for three days. No phase separation even after four freeze and thaw cycles. Solids 15.30%

Example 49

A reduced irritation formulation using SCMI/SCI blend, SLES and Kelzan ST was prepared as follows. The following components were added:

| Ingredient | Amount (% by weight) |
| --- | --- |
| SCMI + SCI (4:6) solid (86.30% active) | 5.00 |
| Empigen BR (A&W, 35%)) | 10.00 |
| Empigen CDR-60 (A&W, 35%) | 5.00 |
| Empicol SDD/UEF (35%) | 3.00 |
| Glycereth 26 | 3.00 |
| KCl solid | 0.50 |
| Water and preservative | qs to 100, | and then all of the components were weighed into a beaker and warmed up to 50-55° C. to dissolve all solids and cooled to about 30° C., and measured viscosity and then added desired preservative. This clear viscous material had a viscosity of 199 cps@ 100 rpm. Spindle#3 and had a pH of 7.18 and was lowered with 20% citric acid to 5.46. Viscosity was increased with KCl to 3713 cps@20 rpm. It remained clear at 7 C for three days. No phase separation even after four freeze and thaw cycles. Solids 15.50%

Example 50

A reduced irritation formulation using SCMI/SCI blend, SLES and Kelzan ST was prepared as follows. The following components were added:

| Ingredient | Amount (% by weight) |
| --- | --- |
| SCMI + SCI (3:7) solid (83.20% active) | 5.00 |
| Empigen BR (A&W, 35%)) | 10.00 |
| Empigen CDR-60 (A&W, 35%) | 5.00 |
| Empicol SDD/UEF (35%) | 3.00 |
| Glycereth 26 | 3.00 |
| KCl solid | 0.50 |
| Water and preservative | qs to 100, | and then all of the components were weighed into a beaker and warmed up to 50-55° C. to dissolve all solids and cooled to about 30° C. and measured viscosity and then added desired preservative. This clear material was mixed with KCl and has a viscosity of 4751 cps@ 20 rpm. Spindle #3 and had a pH of 7.27 and was lowered with 20% citric acid to 5.65. It remained clear at 7 C for three days. No phase separation even after four freeze and thaw cycles. Solids 16.30%

Example 51

A reduced irritation formulation using SCMI/SCI blend, SLES and Kelzan ST was prepared as follows. The following components were added:

| Ingredient | Amount (% by weight) |
| --- | --- |
| SCMI + SCI (2:8) solid (80.60% active) | 5.00 |
| Empigen BR (A&W, 35%)) | 10.00 |
| Empigen CDR-60 (A&W, 35%) | 5.00 |
| Empicol SDD/UEF (35%) | 3.00 |
| Glycereth 26 | 3.00 |
| KCl solid | 0.50 |
| Water and preservative | qs to 100 | and then all of the components were weighed into a beaker and warmed up to 50-55° C. to dissolve all solids and cooled to about 30° C. and measured viscosity and then added desired preservative. This clear material was mixed KCl and has a viscosity of 8242 cps@ 10 rpm. Spindle #3 and had a pH of 7.16 and was lowered with 20% citric acid to 5.50. It remained clear at 7 C for three days. No phase separation even after four freeze and thaw cycles and remained clear at room temperature. Solids 16.16%

Example 52

A reduced irritation formulation using SCMI/SCI blend, SLES and Kelzan ST was prepared as follows. The following components were added:

| Ingredient | Amount (% by weight) |
| --- | --- |
| SCMI + SCI (1:9) solid (83.60% active) | 5.00 |
| Empigen BR (A&W, 35%)) | 10.00 |
| Empigen CDR-60 (A&W, 35%) | 5.00 |
| Empicol SDD/UEF (35%) | 3.00 |
| Glycereth 26 | 3.00 |
| KCl solid | 0.50 |
| Water and preservative | qs to 100, | and then all of the components were weighed into a beaker and warmed up to 50-55° C. to dissolve all solids and cooled to about 30° C. and measured viscosity and then added desired preservative. This clear material was mixed with KCl and has a viscosity of 980° Cps@ 100 rpm. Spindle#3 and had a pH of 7.56 and was lowered with 20% citric acid to 4.95. It remained clear at 7 C for three days. No phase separation even after four freeze and thaw cycles and remained clear at room temperature. Solids 15.60%

While the foregoing was directed to various embodiments of the invention, other and further embodiments of the invention may be devised without departing from the basic scope thereof and the scope thereof is determined by the claims that follow.

What is claimed is:

1. A process for forming a composition of matter, comprising:
   providing a mixture of alkylisethionates and isethionates at a molar ratio of alkylisethionates to isethionates between about 19:1 and about 1:19;
   reacting the mixture with a fatty acid having a carbon chain length between about 4 carbon atoms and about 25 carbon atoms, alternatively between about 6 carbon atoms and about 18 carbon atoms; and
   producing a water soluble composition of isethionate esters with at least 30% solubility, wherein the alkylisethionates are selected from the group consisting of sodium 2-methyl 2-hydroxyethane sulfonate, sodium 1-methyl 2-hydroxyethane sulfonate, sodium 2-ethyl 2-hydroxyethane sulfonate, sodium 1-ethyl 2-hydroxyethane sulfonate, and combinations thereof.

2. The process of claim 1, wherein the fatty acid is selected from the group of saturated fatty acids, unsaturated fatty acids, pure individual fatty acids, and combinations thereof.

3. The process of claim 1, wherein the fatty acid is selected from the group of consisting of coconut oil, tallow, palm kernel oil, butterfat, palm oil, olive oil, corn oil, linseed oil, peanut oil, fish oil, rapeseed oil, and combinations thereof.

4. A composition comprising:
   (i) a first ester anion having the structure:

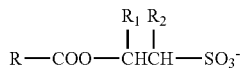

wherein R is a functional group having between about 4 and about 25 carbon atoms; wherein $R_1$ is a straight chain or branched $C_1$ to $C_6$ alkyl group and $R_2$ is a hydrogen atom; and
   (ii) a second ester anion having the structure:

wherein R' is a hydrocarbon group having between about 4 and about 25 carbon atoms, and
   (iii) a third ester anion having the structure:

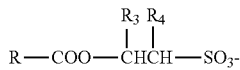

wherein R is a functional group having between about 4 and about 25 carbon atoms; and wherein $R_3$ is a hydrogen atom and $R_4$ is a straight chain or branched $C_1$ to $C_6$ alkyl group.

5. The composition of claim 4, wherein the first ester anion comprises an acyl alkylisethionate ester anion, the second ester anion is an acylisethionate ester anion, and the third ester anion comprises an acyl alkylisethionate ester anion.

6. The composition of claim 4, wherein the composition comprises from about 70 wt % to about 95 wt % acyl alkylisethionate ester anions and from about 5 wt % to about 30 wt % acylisethionate ester anion, and wherein the composition is water soluble.

7. The composition of claim 4, wherein the acyl alkylisethionate ester anions are a sodium cocoyl alkylisethionate ester anions and the acylisethionate ester anion is a sodium cocoyl isethionate ester anion.

8. The composition of claim 4, wherein the melt temperature of the composition ranges from about 170° C. to about 250° C.

9. The composition of claim 4, wherein the melt temperature of the composition ranges from about 180° C. to about 200° C.

10. The composition of claim 4, wherein the first ester anion comprises a cocoyl alkylisethionate ester ion, the second ester anion is a cocoyl isethionate ester anion, and the third ester anion comprises a cocoyl alkylisethionate ester ion.

11. The composition of claim 4, wherein the first ester anion comprises a cocoyl methyl isethionate anion, the second ester ion comprises an cocoyl isethionate anion, and the third ester anion comprises a cocoyl ethyl isethionate anion.

12. The composition of claim 4, wherein a mixture of the first and second ester anion comprises between about 10 wt. % and about 90 wt. % of the composition.

13. The composition of claim 4, wherein R is selected from the group consisting of straight-chain hydrocarbon groups, branched hydrocarbon groups, saturated hydrocarbon groups, unsaturated hydrocarbon groups, and combinations thereof, and R' is selected from the group consisting of straight-chain hydrocarbon groups, branched hydrocarbon groups, saturated hydrocarbon groups, unsaturated hydrocarbon groups, and combinations thereof.

14. The composition of claim 4 further comprising:
   between about 99.50 molar % and about 0.25 molar % of the first and second ester anions; and
   one or more additives selected from the group consisting of: fatty acids, alkyl sulfates, an ethanolamine, an amine oxide, alkali carbonates, water, ethanol, isopropanol, pine oil, sodium chloride, sodium silicate, polymers, alcohol alkoxylates, zeolites, perborate salts, alkali sulfates, enzymes, hydrotropes, dyes, fragrances, preservatives, brighteners, builders, polyacrylates, essential oils, alkali hydroxides, water-soluble branched alkylbenzene sulfonates, ether sulfates, alkylphenol alkoxylates, fatty acid amides, alpha olefin sulfonates, paraffin sulfonates, betaines, chelating agents, tallow amine ethoxylates, polyether amine ethoxylates, ethylene oxide/propylene oxide block copolymers, alcohol ethylene oxide/propylene oxide low foam surfactants, methyl ester sulfonates, alkyl polysaccharides, N-methyl glucamides, alkylated sulfonated biphenyl oxide, polyethylene glycol, and combinations thereof.

15. A personal care cleanser comprising:
(i) a first ester having the structure:

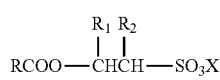

wherein R is a functional group having between about 4 and about 25 carbon atoms; wherein $R_1$ is a straight chain or branched $C_1$ to $C_6$ alkyl group and $R_2$ is a hydrogen atom; wherein X is selected from the group consisting of hydrogen, an alkali metal, an alkaline earth metal, zinc, aluminum, ammonium, ammonium ions substituted with one or more organic groups, and combinations thereof; and (ii) a second ester having the structure:

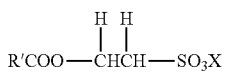

wherein R' is a hydrocarbon group having between about 4 and about 25 carbon atoms; wherein X is selected from the group consisting of hydrogen, an alkali metal, an alkaline earth metal, zinc, aluminum, ammonium, ammonium ions substituted with one or more organic groups, and combinations thereof; and (iii) a third ester having the structure:

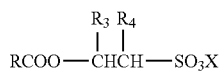

wherein R is a functional group having between about 4 and about 25 carbon atoms; wherein $R_3$ is a hydrogen atom and $R_4$ is a straight chain or branched $C_1$ to $C_6$ alkyl group; wherein X is selected from the group consisting of hydrogen, an alkali metal, an alkaline earth metal, zinc, aluminum, ammonium, ammonium ions substituted with one or more organic groups, and combinations thereof.

16. The personal care cleanser of claim 15, wherein the first ester is an acyl alkylisethionate ester and the second ester is an acylisethionate ester.

17. The personal care cleanser of claim 15, wherein the first ester is a sodium cocoyl alkylisethionate ester and the second ester is a sodium cocoyl isethionate ester.

18. The personal care cleanser of claim 15, wherein the first ester comprises sodium cocoyl methyl isethionate, sodium cocoyl ethyl isethionate, or combinations thereof, and the second ester comprises sodium cocoyl isethionate.

19. The personal care cleanser of claim 15, wherein the cleanser comprises between about 5 wt. % and about 70 wt. % of the first ester and second ester.

* * * * *